US007187968B2

(12) United States Patent
Wolf et al.

(10) Patent No.: US 7,187,968 B2
(45) Date of Patent: Mar. 6, 2007

(54) APPARATUS FOR ACQUIRING AND TRANSMITTING NEURAL SIGNALS AND RELATED METHODS

(75) Inventors: Patrick D. Wolf, Durham, NC (US); Miguel A. L. Nicolelis, Chapel Hill, NC (US); James C. Morizio, Durham, NC (US); John K. Chapin, Brooklyn, NY (US)

(73) Assignee: Duke University, Durham, NC (US)

( * ) Notice: Subject to any disclaimer, the term of this patent is extended or adjusted under 35 U.S.C. 154(b) by 252 days.

(21) Appl. No.: 10/692,235

(22) Filed: Oct. 23, 2003

(65) Prior Publication Data

US 2005/0090756 A1    Apr. 28, 2005

(51) Int. Cl.
    *A61B 5/04* (2006.01)
(52) U.S. Cl. .................... 600/544; 600/545
(58) Field of Classification Search ............ 600/545, 600/544; 623/25
    See application file for complete search history.

(56) References Cited

U.S. PATENT DOCUMENTS

| | | | | |
|---|---|---|---|---|
| 3,821,949 A | * | 7/1974 | Hartzell et al. ............ 600/545 |
| 3,924,606 A | * | 12/1975 | Silva et al. ............... 600/547 |
| 4,478,223 A | * | 10/1984 | Allor ......................... 600/512 |
| 4,846,190 A | * | 7/1989 | John .......................... 600/544 |
| 5,222,503 A | * | 6/1993 | Ives et al. ................. 600/544 |
| 5,275,172 A | * | 1/1994 | Ives .......................... 600/544 |
| 6,984,205 B2 | * | 1/2006 | Gazdzinski ............... 600/160 |
| 2003/0025604 A1 | * | 2/2003 | Freeman ................. 340/573.1 |
| 2003/0093129 A1 | * | 5/2003 | Nicolelis et al. ............. 607/45 |
| 2004/0082875 A1 | * | 4/2004 | Donoghue et al. .......... 600/544 |

* cited by examiner

*Primary Examiner*—Charles Marmor, II
*Assistant Examiner*—Patricia Mallari
(74) *Attorney, Agent, or Firm*—Jenkins, Wilson, Taylor & Hunt, P.A.

(57) ABSTRACT

Neurochip for Neuroprosthetic Control. According to one embodiment, a neural spike detection system is provided. The neural spike detection system can include a signal receiver operable to receive a plurality of neural signals including neural spikes. The system can also include a neural spike detector adapted to communicate with the signal receiver and detect neural spikes in the plurality of neural signals. Further, the system can include a transmitter connected to the neural spike detector and operable to transmit an information signal when a neural spike is detected.

38 Claims, 16 Drawing Sheets

APPARATUS FOR ACQUIRING AND TRANSMITTING NEURAL SIGNALS AND RELATED METHODS

GRANT STATEMENT

This invention was supported by DARPA grant N0014-98-1-0676. Thus, the Government has certain rights in this invention.

TECHNICAL FIELD

The present invention relates generally to apparatus for acquiring and transmitting neural signals for processing. Specifically, the present invention relates to a system for acquiring neural signals having neural spikes and transmitting an information signal in response to detecting a neural spike.

BACKGROUND ART

The human brain is an exceedingly complex processing system, which integrates continual streams of incoming sensory input data with stored memories, uses the input data and memories in complex decision processes at both conscious and unconscious levels and, on the basis of these processes, generates observable behaviors by activation of its motor or movement control pathways and the muscles which these innervate. The neurons of the nervous system propagate input data by generating characteristic electrical pulses called action potentials, or neural spikes, that can travel along nerve fibers. A single neuron or a group of neurons represent and transmit information by firing sequences of neural spikes in various temporal patterns. Information is carried in the neural spike arrival times.

In certain cases of traumatic injury or neurological disease, the brain can be partially isolated from the periphery. Input data from certain senses are thus lost, at least for a portion of the body, as are many voluntary movements. Spinal cord injury is a well-known example of traumatic injury. With spinal cord injury, the pathways that link higher motor centers in the brain with the spinal cord and that are used for control of voluntary movements can be functionally transected at the site of injury. As a result, the patient is paralyzed, and can no longer voluntarily activate muscles that are innervated by regions of the spinal cord below the level of the injury. Despite the injury to their long fibers, however, many of the cells in these higher brain regions that control voluntary movement will survive and can still be activated voluntarily to generate electric signals for controlling voluntary movement. By recording the electrical activities produced from these cells with implantable neural sensors (e.g., a microwire electrode array, a microwire, a magnetic field detector, chemical sensor, or other neural sensor), signals generated by the cells can be "exteriorized" and used for the control of external prostheses, such as an assist robot or an artificial limb, or functional electrical stimulation paralyzed muscles. Additionally, these generated signals can be used for control of computer operations such as the movement of a cursor on a computer display.

Another example of such loss occurs in cases of amyotrophic lateral sclerosis (Lou Gehrig's Disease), in which the motor neurons that control muscles, as well as some of the brain cells that control these motor neurons, degenerate. In advanced stages of this disease, the patient might have completely intact senses and thought processes, but is "locked in," so that neither movements nor behavioral expressions of any kind can be made. Providing these patients with some way of communicating with the external world would greatly enhance their quality of life.

In sum, there is a need to develop a system for monitoring and processing the electrical signals from neurons within the central nervous system, so that the brain's electrical activity can be "exteriorized" and used for the voluntary control of external prostheses or assist devices which are adapted to provide sensory feedback. In this way, damaged pathways can be circumvented and some control of the environment can be restored; additionally, a patient can be provided the ability to interact with his or her environment. Because the electrical fields of small groups of neurons drop off rapidly with distance from the cells, a representative system can include surgically implanted electrodes or other neural sensors, which can be placed in close proximity to the individual or large numbers of brain cells that generate command signals for voluntary movement.

Neural signals can be detected by measuring the electric field potential of an area or region of the brain or other organ. The field potential detected at any one point represents the sum of the potential created by a number of electric potential generators in the area surrounding the field potential measuring device. By way of example, when an individual monitors a field potential (e.g., the amplitude of a field potential) at a point on the surface of the cerebral cortex, for example, what is detected is the overlapping summation of electric fields generated by active neurons in the depths of the cerebral cortex, which have spread through the tissues and up to the surface. These nerve cells can be characterized as point dipoles that are oriented perpendicular to the surface of the cerebral cortex. In other words, each cell or group of cells has a current source where positive charge moves outwardly across its membrane and a current sink where the same amount of positive charge moves inwardly at each instant. Thus, the flow of current across each cell or group of cells establishes an electric field potential that is equivalent to the electrostatic field potential of a pair of point charges, one positive at the location of the current source and one negative at the current sink. The amplitude of this field potential, i.e., the electric field strength, decreases inversely with distance in all directions from each point charge, and is relatively low at the surface of the cerebral cortex.

When many nerve cells are generating field potentials in a given region, these field potentials sum and overlap in the neural tissue, in the extracellular fluid, and at the brain surface. This summation is a linear function in this volume conductor, since the field strength of a given cell or group of cells varies inversely as a function of the distance from each current source or sink. Thus, if the electric potential of a given region of neurons is measured at a sufficient number of points and depths, it is possible to deduce the locations and amplitude of each dipole generator at any instant of time.

Integrated circuits, called neurochips, have been developed to acquire neural signals from a subject and condition the signals for processing. Some current neurochips include multi-channel sieve electrodes for detecting neural signals from regenerated axons. A sieve electrode is a planar structure with small throughbores extending therethrough. In order to implant a sieve electrode, an axon is severed, the ends placed through adjacent throughbores, and the nerve is allowed to heal. Signals in the regenerated axon are detected by the sieve electrode. Detected signals are then processed and transmitted by the neurochip for further processing.

Many current neural signal systems utilize radio frequency telemetry for transmitting information signals. A significant amount of the total power required for operating a neurochip is used to implement telemetry. High power consumption is undesirable for neurochips in order to achieve reduced neurochip and system size. Thus, neurochip telemetry and transmission methods are desired having lower power requirements for transmitting information signals. In general, double the power is required to transmit twice the amount of data. Thus, neurochips are desired that require as little data transmission as possible, thus using a lower amount of power to transmit. Further, neurochips are desired having a smaller size and improved circuitry for receiving, conditioning, and processing neural signals. Such improvements will reduce the amount of information that must be passed to through the telemetry links to other parts of the device thus conserving power and will distribute the processing burden to multiple devices operating serially and synchronously.

DISCLOSURE OF THE INVENTION

According to one embodiment, a neural spike detection system is provided. The neural spike detection system can include a signal receiver operable to receive a plurality of neural signals comprising a neural spike. The system can also include a neural spike detector adapted to communicate with the signal receiver and detect the neural spike in the plurality of neural signals. Further, the system can include a transmitter in communication with the neural spike detector and operable to transmit an information signal when a neural spike is detected.

According to a second embodiment, a neural signal detection system is provided. The neural signal detection system can include a signal receiver adapted to condition neural signals received from neural sensors. The system can also include a control module operable to select neural signals for transmission. Further, the system can include a transmitter operable to transmit the conditioned neural signals selected by the control module.

According to a third embodiment, a neural signal transmission system is provided. The system can include a signal receiver operable to condition a plurality of neural signals. The system can also include a wireless power receiver adapted to wirelessly receive power from a wireless power transmitter for powering the system. Further, the system can include a neural signal transmitter operable to transmit the conditioned neural signals.

According to a fourth embodiment, a method for transmitting a neural spike signal is provided. The method includes receiving a neural signal including neural spikes and detecting occurrences of neural spikes in the neural signal. The method can also include transmitting an information signal indicating the occurrence of a neural spike when a neural spike is detected.

According to a fifth embodiment, a method for transmitting neural signals is provided. The method can include selecting neural signals received by neural sensors for transmission. The method can also include conditioning the selected neural signals. Further, the method can include transmitting the neural signals.

According to a sixth embodiment, a method for transmitting neural signals is provided. The method can include conditioning a plurality of neural signals. The method can also include receiving a wireless power signal from a wireless power transmitter for powering the system. Further, the method can include transmitting the neural signals.

According to a seventh embodiment, a neural processing system is provided. The system can include an implanted neurochip operable to transmit a plurality of detected neural signals including neural spikes and noise. The system can also include a wearable relay device operable to receive the plurality of detected neural signals, filter the noise, and transmit a signal having the neural spike. Further, the method can include a remote processing system operable to receive the signal having the neural spike.

According to an eighth embodiment, a neural signal receiver for conditioning a plurality of neural signals is provided. The neural signal receiver can include a plurality of preamplifiers for conditioning the plurality of neural signals. The neural signal receiver can also include a differential amplifier module connected to the plurality of preamplifiers for selecting a reference signal from among the plurality of neural signals and generating a plurality of difference signals. The plurality of difference signals can be a difference between the plurality of neural signals and the reference signal.

Some of the objects of the invention having been stated hereinabove, other objects will become evident as the description proceeds when taken in connection with the accompanying drawings as best described hereinbelow.

BRIEF DESCRIPTION OF THE DRAWINGS

Exemplary embodiments of the invention will now be explained with reference to the accompanying drawings, of which.

DETAILED DESCRIPTION OF THE INVENTION

I. Definitions

Figure 1:
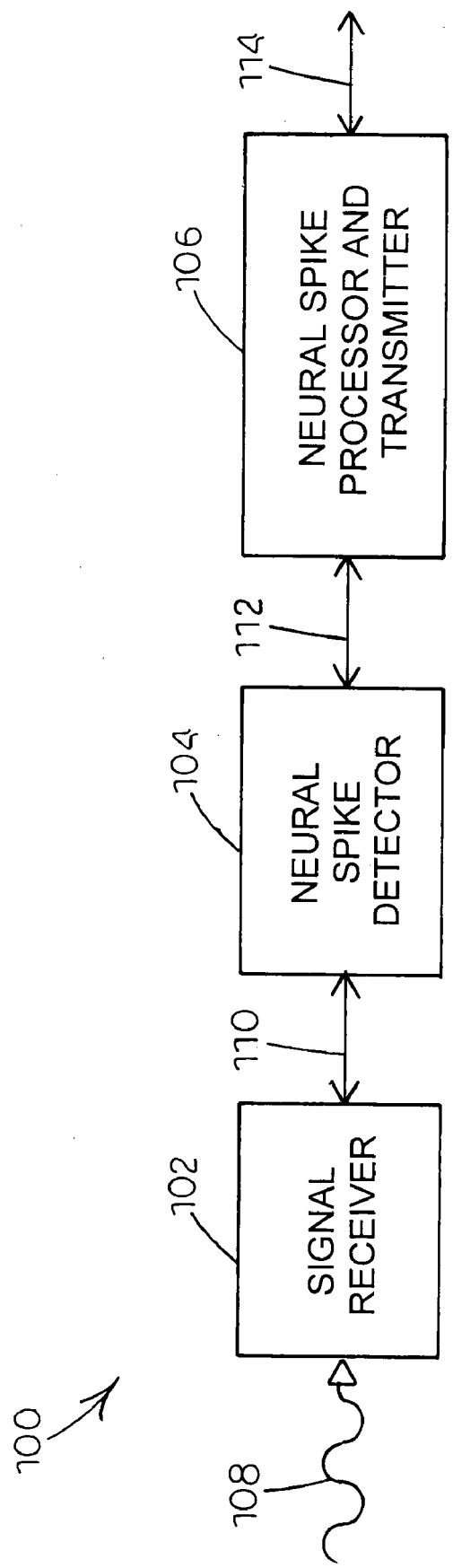
FIG. 1 is a schematic view of a neural signal system according to an embodiment of the present invention.

Following long-standing patent law convention, the terms "a" and "an" mean "one or more" when used in this application, including the claims.

As used herein, the term "about," when referring to a value or to an amount of mass, weight, time, volume, concentration or percentage is meant to encompass variations of ±20% or ±10%, more preferably ±5%, even more preferably ±1%, and still more preferably ±0.1% from the specified amount, as such variations are appropriate to perform the disclosed method.

As used herein, the terms "actuator", "external device" and "prosthetic limb" are used interchangeably and mean any kind of device adapted to perform a movement. Although an actuator preferably performs a movement in three dimensions, an actuator can also be limited to performing movements in two dimensions. Thus, an actuator can be a manipulandum confined to two-dimensional motion. A representative actuator comprises a prosthetic limb, which can be fitted on, or integrated into, the body of a subject. An actuator can also be associated with machinery and/or circuitry that allow the actuator to respond to one or more forms of input with one or more movements. In one example, the range of motion of an actuator designated as a substitute for a patient's lost or paralyzed limb is limited to the range of motion of the limb for which the actuator is substituting.

As used herein, the term "electrode" means an electric conductor through which a voltage potential can be measured. An electrode can also be a collector and/or emitter of an electric current. In one embodiment, an electrode is a solid and comprises a conducting metal. Representative conducting metals include noble metals, alloys and particularly stainless steel and tungsten. An electrode can also be a microwire, or the term "electrode" can describe a collection of microwires. In one embodiment, electrodes comprise polytetrafluoroethylene (PTFE) (TEFLON®, a product produced by E.I. Du Pont de Nemours and Company) coated stainless steel or tungsten microwires.

As used herein, the terms "field potential data" and "field potentials" are used interchangeably and typically mean low frequency, voltage measurements collected from one or more locations near or at one or more neurons in a subject's brain or nervous system.

As used herein, the term "integrated circuit" refers to a small-scale, electronic device densely packaged with more than one integrated, electrical component. The components are manufactured on the surface of semiconductor material. There are various scales of integrated circuits that are classified based on the number of components per surface area of the semiconductor material, including small-scale integration (SSI), medium-scale integration (MSI), large-scale integration (LSI), very large-scale integration (VLSI), ultra large-scale integration (ULSI).

As used herein, the term "location source" means a position wherein a neural sensor can detect one or more neural signals.

As used herein, the term "neural signal" means a signal, which can take any form, originating in the nervous system of an organism. Neural signals typically include neural spike signals that carry information in their arrival times at destination neurons.

As used herein, the term "neural sensor" means an implantable device for sensing neural signals. Examples of neural sensors include microwire electrode arrays, optical sensors, microwires, magnetic field detectors, chemical sensors, and other suitable neural sensors which are known to those of skill in the art upon consideration of the present disclosure.

As used herein, the term "neurochip" means any integrated circuit, multi-integrated circuit, or multi-module system adapted for detecting neural signals from the body of an organism. In one embodiment, a neurochip is adapted to be implanted in an organism near the nervous system for detecting neural signals.

As used herein, the terms "operator," "patient" and "subject" are used interchangeably and mean any individual monitoring or employing the present invention, or an element thereof. Operators can be, for example, researchers gathering data from an individual, an individual who determines the parameters of operation of the present invention or the individual in or on which a high-density multichannel microelectrode array is disposed. Broadly, then, an "operator," "patient" or "subject" is one who is employing the present invention for any purpose. As used herein, the terms "operator," "patient" and "subject" need not refer exclusively to human beings, but rather the terms encompass all organisms having neural tissue, such as monkeys, dogs, cats, rodents, etc.

II. General Considerations

Through the years there has been significant research in the area of detecting and observing various electric potentials generated within the human body for medical diagnosis, biofeedback control of mental and physical states, and control of external devices. It is known that different regions of the brain are used to control different parts of the body and to process different sensory inputs. It is also known that when a human performs a certain function, such as moving an extremity or listening to a particular sound, multiple regions of the brain generate electrical action potentials to accomplish that function. It is also known that direct electrical stimulation of a particular region of the brain can cause at least partial reproduction of the functions or sensory input normally associated with that region of the brain. Determining which portions of a patient's brain are responsible for certain motor activities or certain sensory functions has become known as brain "mapping." After a patient's brain has been mapped, the brain can be electrically stimulated to restore lost functions.

For example, it is possible to determine which portions of a patient's brain are responsible for processing signals associated with the movement of an extremity. Once a neurologist knows which portions of the patient's brain are responsible for processing these signals, it is possible to electrically stimulate selected portions of the patient's brain to cause the patient to "move" the extremity. Thus, a patient whose motor control has been partially or permanently damaged can regain motor control if an apparatus is employed to translate these neural signals into movement of an external device, such as an actuator. Similarly, if the areas of the patient's brain that are associated with tactile and other sensory information are known, these areas of the patient's brain can be electrically stimulated to make the patient "experience" the sensory interaction between an object and an external device interacting with the object. Systems according to the present invention can be employed as a component of a system such as a closed loop brain-machine interface or intelligent brain pacemaker. These devices can greatly enhance the quality of life of individuals those individuals whose motor control has been impaired.

III. Configuration and Operation of the Neural Signal System

In accordance with the present invention, efficient methods and systems are provided for detecting, processing, and transmitting information contained in neural signals received from neural tissues, for example neural tissue of the brain or central nervous system. This stored information can be used to control an external device, such as an actuator, prosthetic device, or computer system, or to treat a neurological condition. The methods and systems according to the present invention will be explained in the context of flow charts and diagrams. It is understood according to this invention that the flow charts and diagrams can be implemented in hardware, software, or a combination of hardware and software. Thus, the present invention can include computer program products comprising computer-executable instructions embodied in computer-readable media for performing the steps illustrated in each of the flow charts or implementing the devices illustrated in each of the diagrams. FIG. 1 is a schematic view of a neural signal system of the present invention, generally designated 100, according to one embodiment of the present invention. Broadly, neural signal system 100 includes the following main modules: a signal receiver 102, a neural spike detector 104, and a neural spike processor and transmitter 106.

While in operation, signal receiver 102, described in more detail below, detects neural activity in the form of field potential data 108 generated from neural tissue (e.g., from large numbers of single neurons) in a subject, such as a human or a monkey. Signal receiver 102 converts field potential data 108 to an electrical-based representation of the neural signal that is suitable for processing by the hardware and/or software of system 100. Signal receiver 102 can include one or more neural sensors (e.g., metallic wire electrodes) implanted in a location in the subject for detecting field potential data 108 of the neural signals of interest. In one embodiment, signal receiver 102 can include multiple neural sensors that are positioned in different location sources in the subject for converting the field potential data detected from different neurons into electrical-based neural signals.

Signal receiver 102 can also include electrical components for conditioning the electrical-based neural signals. Preferably, signal receiver 102 conditions the electrical-based neural signal with buffering and filtering to remove unwanted in-band and out-of-band signal noise, such as field potential data detected from signals of other bioelectric generators in the subject. These sources include the heart (ECG), muscles (EMG), and signals from the effect of mechanical movement of the sensor in response to blood pressure, respiration, and physical motion. Further, signal receiver 102 can correct a DC offset problem associated with conditioning neural signals. Further, system 100 can include a transmission link 110 for communicating amplified and conditioned, electrical-based, neural signals on one or more communication channels from signal receiver 102 to neural spike detector 104.

Neural spike detector 104 can receive one or more conditioned signals on one or more communication channels from signal receiver 102 for detecting the occurrence of a neural spike in any of the conditioned signals. Additionally, neural spike detector 104 can include spike sorting, the process of identifying which particular neuron detected on a conditioned signal produced a particular neural spike. Neural spike detector 104 can detect a neural spike and sort detected spikes in a conditioned signal by performing a mathematical algorithm. In one embodiment, the mathematical algorithm can detect a neural spike on a conditioned signal by the following steps: (1) sampling the conditioned signal; (2) combining the samples; (3) comparing the combined samples to predetermined thresholds; and (4) determining whether a spike has been detected based on the comparison in step (3). The comparison can be to one threshold value, for instance a voltage level, or could be multiple threshold values, for instance level and slope, or could be the level of a derived signal, for example, energy or absolute value, or the level of multiple derived signals. Similarly, the detector may differentiate between threshold crossings in the positive direction and the negative direction. Upon detecting a neural spike, neural spike detector 104 can transmit an information signal to neural spike processor 106 to indicate the detection of a neural spike in one of the conditioned signals. Neural spike detector 104 can transmit information signals to neural spike processor 106 via transmission link 112. When neural signals are received from multiple channels or locations, the information signal can carry data identifying the neuron corresponding to a detected neural spike.

Neural spike processor 106 can receive the information signal from neural spike detector 104 and generate and transmit control signals based on the information signals. Control signals can be transmitted via a transmission link 114 to a device such as an actuator, prosthetic device, computer system, or other suitable device. Other devices include but are not limited to weapons or weapon systems, robots or robot systems, other commercial electronic devices that can be controlled remotely including TV, radio, mechanical bed systems stoves, ovens, and other cooking devices, other household devices that might be controlled by a remote device and used to improve the quality of life of a disabled person. Still other devices include scientific or commercial mechanical devices that work at a much larger or much smaller scale than is normal for a human, for instance optical tweezers for manipulating molecules and atoms, or earth moving equipment. Preferably, transmission link 114 comprises a wireless link such as ultra wide band (UWB) radio telemetry. Alternatively, the transmission link can comprise any other suitable wireless link such as by the BLUETOOTH™ standard developed by BLUETOOTH SIG, Inc. Neural spike processor 106 can include a memory for storing information signals. Data can be stored in terms of the time the neural spike was generated and/or the channel or location source of the neural spike. The memory can also receive and store the signal data with information identifying the sensory or motor activity ongoing at the time of the neural spike. In one embodiment, the memory stores the signals in a digital format. Alternatively, signal data can be represented by analog voltage records of the complete signal, a time multiplexed analog signal, analog records of only the neural spikes and a time indicator identifying the time of the neural spike, or any other suitable format known to those of skill in the art.

According to one embodiment, neural signal system 100 can also be operable to receive signals for configuring the components of system 100, as described herein. Therefore, in this embodiment, links 110, 112, and 114 comprise bidirectional signals for passing configuration data.

In one embodiment, neural signal system 100 comprises a neurochip, an integrated device or a highly integrated package of semiconductor circuits adapted to receive signals from the neural tissue of a subject and process and condition neural signals. The neurochip can be implanted in the tissue of a subject or positioned outside the skin of the subject in a transcutaneous configuration. Alternatively, the neurochip can be positioned at a location on or near the subject and can be adapted to interact with additional components, such as a signal receiver, via a conductive wire or wireless communication. The processing by the neurochip can be analog signal processing or digital signal processing. The neurochip can be implemented using a VLSI circuit. The use of integrated circuit technology allows the tailoring of device parameters to optimally use the available power and space for the desired sensory or motor functions.

In an alternative to the implementation of components 102, 104, and 106 on a single neurochip for implantation in a subject, signal receiver 102 and neural spike detector 104 can be implemented on a neurochip, and neural spike processor 106 can be implemented separately as a non-implanted, integrated circuit. Further in the alternate, components 102, 104, and 106 of neural signal system 100 can be implemented together or separately on a single integrated circuit, any combination of one or more integrated circuits, or any other suitable hardware and/or software combination known to those of skill in the art.

In one embodiment, signal receiver 102 is implemented in the form of an implant. Alternatively, one or more of components 104 and 106 can be implemented as an integrated circuit in the form of an implant, a transcutaneous implant, a remote device, a portable remote device, a wearable device, or a wearable tethered device. An implant is a component residing completely within the subject. A transcutaneous implant is an implanted component having a mechanical transcutaneous link, such as a transcutaneous, conductive wire, or to a component located outside of the skin of the subject. A remote device is a component remotely located from the subject. Typically, the remote device does not physically move with the subject. Alternatively, the remote device can move with the subject without being wearable by the subject. A wearable device is a component wearable by a subject, removed with no surgical procedure, and not physically connected to a remote device. For example, a wearable device can be worn on the head, back, waist, or other convenient location on the subject (e.g., a helmet or backpack). A wearable, tethered device is a wearable device that is connected to a remote device via a wire link.

Components can be implemented as a combination of one or more implants, transcutaneous implants, remote devices, portable remote devices, wearable devices, or wearable tethered devices. In one exemplary embodiment, signal receiver 102 can be implemented as a transcutaneous implant that communicates with a wearable, tethered neural spike detector 104 located on the head of a subject. In another exemplary embodiment, signal receiver 102 is implemented as an implant communicating via a wire link with a wearable neural spike detector 104. Wearable neural spike detector 104 communicates with another wearable system including neural signal processor 106 on the waist of a subject. Neural signal processor 106 can transmit via radio communication to a remote device for further interpretation.

As stated above, transmission links 110, 112, and 114 can be implemented as a wire link, a wireless link, or a combination of wire and wireless links. The following list includes exemplary embodiments of neural signal system 100 having different wire and wireless link configurations according to the present invention:

According to one embodiment, neural signal system 100 includes an implanted component, such as a neurochip, and a remote component, such as a processing system. The implanted component transmits signals to the remote component via a wireless link.

According to one embodiment, neural signal system 100 includes a wearable component, a transcutaneous implant, such as a neurochip, and a remote component, such as a computer processing system. The transcutaneous implant communicates with the wearable component via a wire link. The wearable component communicates to the remote component via a wireless link.

According to one embodiment, neural signal system 100 includes an implanted neurochip, a wearable component, and a remote component. The implanted neurochip transmits signals to the wearable component via a wireless link. The wearable component transmits signals to the remote component via a wire link.

According to one embodiment, neural signal system 100 includes an implanted component having a set of transcutaneous wires. System 100 also includes a wearable component, such as a neurochip disposed in a helmet. The neurochip and implanted component communicate via a wireless link. Further, the wearable component transmits signals to a second wearable component via a wireless link. The second wearable component is tethered to a remote or portable remote component for wire communication. Alternatively, the second wearable component can transmit control signals to an actuator.

According to one embodiment, neural signal system 100 includes an implanted component, such as a neurochip, operable to transmit signals via a wireless link. The wireless link transmits signals optically to a wearable component, such as a helmet. The wearable component is operable to relay signals to a remote component for further processing.

According to one embodiment, neural signal system 100 includes a remote component operable to transmit data acquisition configuration parameters to an implanted component.

According to one embodiment, neural signal system 100 includes an implanted neurochip for transmitting via a wireless link, such as optically, to a wearable component including a transmitter. The transmitter transmits via a wireless link, such as a radio link, to a remote component. The remote component transmits via a radio link to a wearable prosthetic device.

According to one embodiment, neural signal system 100 includes an implanted component, such as a neurochip, for optically transmitting signals to a wearable component. The wearable component communicates with a wearable component, such as a prosthetic device, via a conductive wire.

According to one embodiment, neural signal system 100 includes an implanted, transcutaneous component, such as a set of implanted transcutaneous wires, operable to transmit signals to a wearable component having a neurochip. The wearable component transmits control signals to a wearable component, such as a wearable prosthetic device.

III.A. Receiving Neural Signal

A method for receiving neural signals in neural signal system 100 according to the present invention can be performed by signal receiver 102. The purpose of receiving neural signals is to convert a biological-based neural signal into an electrical-based, machine-readable signal and to condition the received signal. In one embodiment, neural signal detection according to the present invention includes two main steps—(1) receiving the biological-based neural signal from a neuron of interest and (2) conditioning the neural signal. A transmission step optionally can be included if transmission link 110 is necessary for transmitting the conditioned signal from neural signal receiver 102 to neural spike detector 104.

The step of receiving the neural signal can include providing a neural sensor near a neuron to obtain a neural signal in the form of field potential data from a neuron or large number of single neurons. The neural sensor converts the field potential data to electrical-based current flow. The typical maximum potential voltage associated with a propagating neuronal action potential is between approximately 100 and 700 microvolts (μV). The chemical reaction that performs this conversion requires a driving potential, referred to as polarization, that causes a significant direct current (DC) voltage of approximately 200 millivolts (mV) on the measured neural signals. Because the offset voltage is a function of the ionic concentrations at the interface, small movements in the neural sensor associated with respiration, blood pressure, and locomotion can modulate the DC potential providing an additional source of electrical noise. The DC and low frequency noise components of the measured electrical-based signal are frequently orders of magnitude greater in size than the neural signals of interest.

Isolating the neural signal is one of the primary challenges in building an integrated circuit for this purpose. The neural sensor in the subject can be situated among thousands of neurons and thus measures neural spikes from many neurons simultaneously. Only a few neurons produce signals with amplitude large enough to be accurately interpreted. The remaining neurons produce signals that are interpreted as noise. The neural information carried by the neural spike is contained in its timing relative to other neural spikes from the same neuron. Thus, it is important to be able to differentiate spikes originating from a specific neuron or neurons. Neural spike sorting schemes for identifying the neuronal origin of a given neural spike can be implemented in hardware and/or software. Typically, neural spike sorting schemes require the entire temporal waveform of the approximately 1–2 millisecond (ms) neural spike to be acquired and analyzed by the system.

Conditioning the electrical-based signal can include the steps of filtering and differential recording the detected signal. As stated above, the electrical signal of interest is a neural spike approximately 2 milliseconds (ms) in duration. The frequency content of the neural spike can be between approximately 500 and 8000 Hertz. This relatively small voltage spike is corrupted by several sources of noise both internal and external. Some significant sources of corruption is from other bioelectric generators within a subject, such as cardiac, neuromuscular, and other cortical neurons located in proximity to the electrodes. Filtering and differential recording eliminates sources of out-of band noise or noise in frequencies outside the frequencies of interest. Differential recording eliminates in-band noise common to both the signal and its reference voltage.

III.B. Neural Spike Detection

A method for neural spike detection in neural spike detector 104 according to the present invention includes receiving conditioned neural signals and detecting neural spikes in the conditioned signals. Neural spike detector 104 can also include sorting spikes according to the particular neuron producing a detected spike. As discussed above, neural spike detector 104 can detect neural spikes among noise signals by threshold and slope detection. In one embodiment, neural spike detection includes four main steps—(1) sampling the conditioned signal; (2) combining the samples; (3) comparing the combined samples to predetermined thresholds; and (4) determining whether a spike has been detected based on the comparison in step (3). One such process can digitally filter the signal to produce a measure of slope and detect the location of a slope above or below a particular value that corresponds in time with a voltage level exceeding a particular value.

Figure 2:
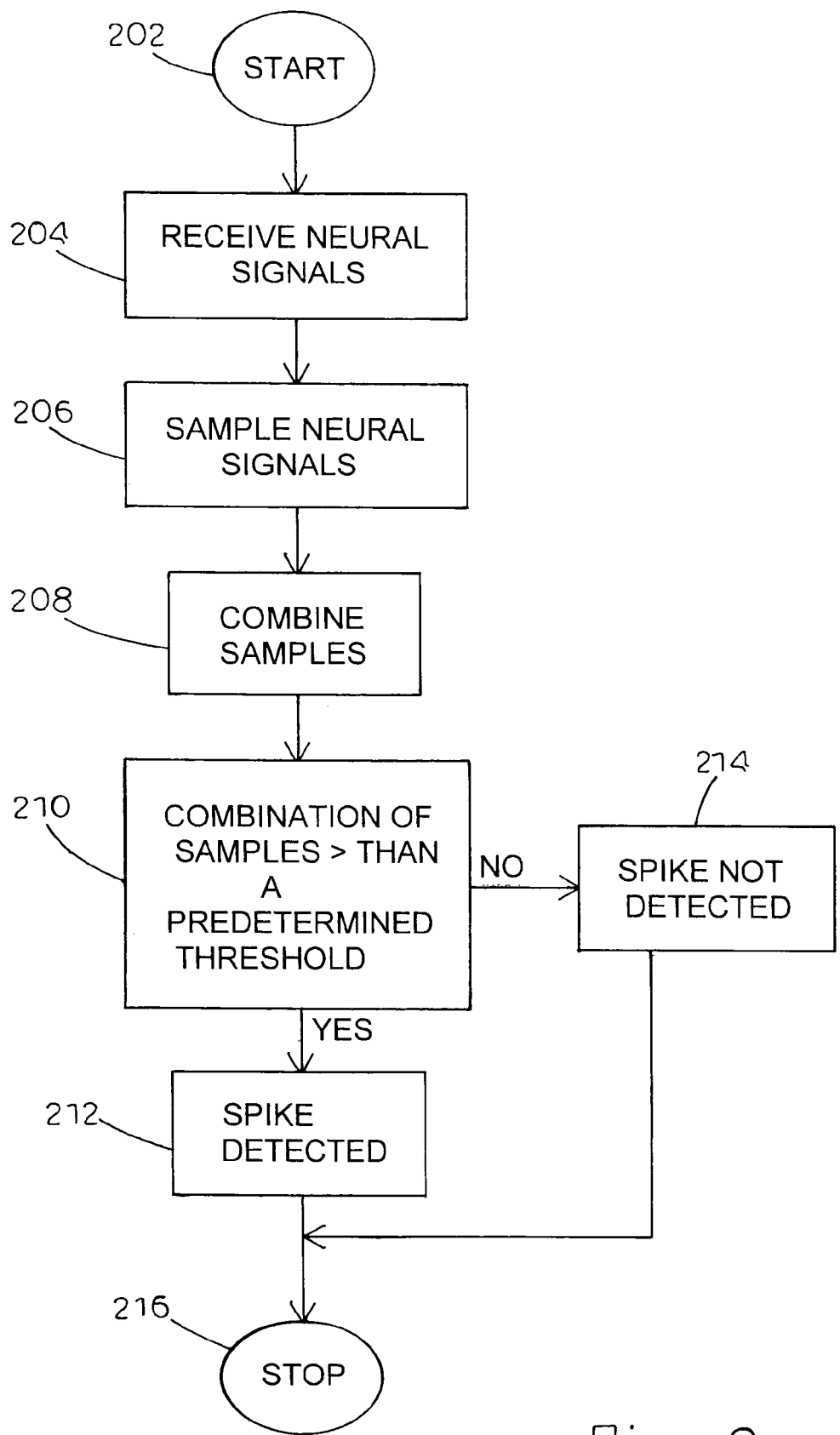
FIG. 2 is a flow chart of a process for neural spike detection according to an embodiment of the present invention.

Referring to FIG. 2, a flow chart is provided which illustrates a process for neural spike detection according to an embodiment of the present invention. As stated above, such neural spike detection can be performed by neural spike detector 104. The process begins at the step indicated by reference numeral 202. At step 204, neural signals are received by neural spike detector 104. The received neural signals can be electrical-based analog signals. Next, at step 206, the neural signals can be sampled N times. In one embodiment, the neural signal is sampled 8 times at 40 kHz. The N samples can be combined at step 208. In one embodiment, the samples are combined using gain. Alternatively, the samples can be combined by summing, power operations or other suitable methods known to those of skill in the art. Next, at step 210, it is determined whether the samples are greater than a predetermined threshold. The comparisons can be made to determine the presence of a particular feature of a spike, for example, the point at which the slope or the amplitude or the energy exceeds a threshold. This point can then be taken as the time the spike occurred or some temporal displacement from that point is taken as the time the spike occurred (i.e., 1 millisecond earlier). If the samples are greater than the predetermined threshold, a spike is detected (step 212). If the samples are not greater than the predetermined threshold, a spike is not detected (step 214). Next, the process stops (step 216). The process can then repeat for another sample group at step 202.

Figure 3:
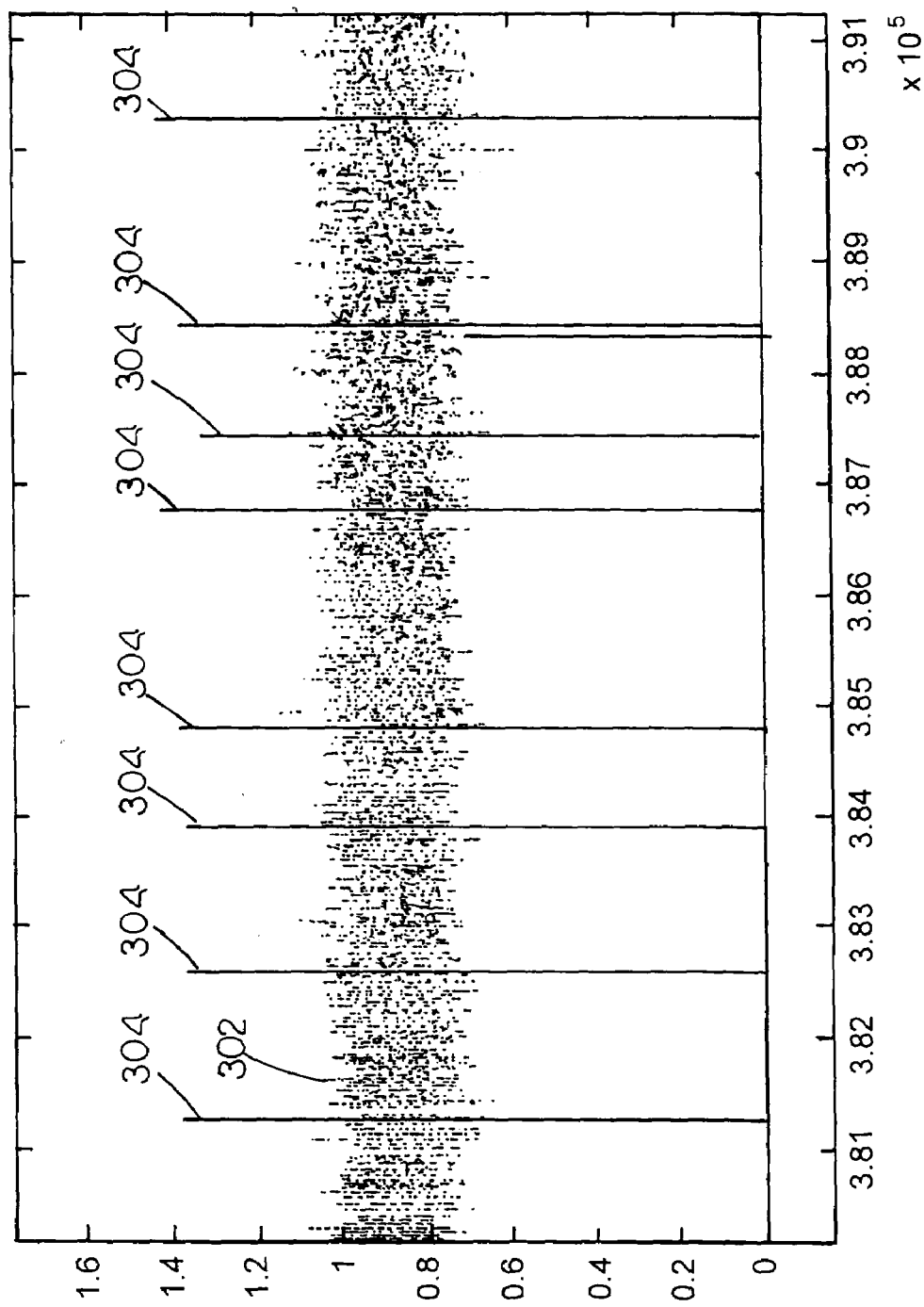
FIG. 3 is a graphical view of simulation results of the input signal and output signal of a neural spike detector according to an embodiment of the present invention.

Referring to FIG. 3, a graphical view of computer simulation results are provided of the input signal and output signal of a neural spike detector 104 according to one embodiment of the present invention. The vertical axis indicates the amplitude of a neural signal. The horizontal axis indicates time. In this embodiment, neural spike detector 104 can determine whether a neural spike is starting to occur based on a number of samples of a neural signal. First, neural spike detector 104 samples a neural signal, obtaining 8 sequential values. Next, neural spike detector 104 determines a neural spike is starting if the sum of the last two samples is less than 0.23 times the sum of the first six samples. Reference numeral 302 indicates the neural signal input to neural spike detector 104. Reference numerals 304 indicates instances of spike detection. In the simulation of this embodiment, 99.97% of all neural spikes in the simulation were detected. Neural spike detector 104 of this embodiment indicated neural spikes falsely about half of the time. These computer simulations were conducted using the MATLAB® mathematics computer program, produced by MathWorks, Inc. of Natick, Mass.

Neural spike detection and sorting can be performed with either analog or digital circuitry. An integrated monolithic analog circuit can detect spikes and pass the reduced data on to a sorter before or after a telemetry link. Alternatively, a monolithic analog circuit can process the detected spikes and perform spike sorting. Further, in the alternative, spike detection and sorting can be performed by digital circuitry by digitizing the neural signals and processing the resultant digital data stream using a digital signal processor or a custom digital circuit.

Upon detecting a neural spike, neural spike detector 104 can indicate the detection of a neural spike on one or more of the communication channels to neural spike processor 106. If necessary, neural spike detector 104 can transmit an information signal to neural spike processor via transmission link 112. When neural signals are received from multiple channels or locations, the information signal can carry data identifying the channel or location source corresponding to the detected neural spike. Further, if spike sorting is performed before transmission on transmission link 112, the information signal can carry information indicating the particular neuron originating the neural spike.

III.C. Neural Spike Processor, Transmitter, and Receiver

A method for neural spike processing and transmission according to the present invention can be performed by neural spike processor 106. The purpose of neural spike processing and transmission is to generate and transmit information or control signals to a suitable device such as an actuator, prosthetic device, or computer system. In one embodiment, the information or control signals are transmitted via a wireless link.

Signal processing of various types can occur. This processing is divided into two stages: 1) processing within one signal 2) processing across many or all signals. In the first stage, the signals can be used with sorting or without sorting. A sorting process generally increases the number of signals by separating portions of one signal into one or more additional signals of spike data. In the second stage, an estimate of firing rate can be made based on a summing of spike counts over an interval (binning) for example at 100 milliseconds. Other methods of estimating rate are familiar to those skilled in the art. Similarly, a process can use the temporal order of the signals to derive other parameters for use in control processing. Such time based interpretation schemes are also known to those skilled in the art. After extraction of the information from a single channel of spikes, the information among signals can be combined. The signals can be combined with linear weighting schemes or using techniques such as neural networks.

As stated above, component 106 can communicate over transmission link 114 via a wireless link. A wireless link is desirable because a subject can move freely within the transmission range of the wireless link. In one embodiment, the wireless link is implemented with ultra wide band (UWB) radio. UWB radio is particularly suited to digital data transmission at high bandwidth (data rates) over short distances. The advantages of UWB radio over other communication systems include low power per bit of information and simplicity of transmission electronics.

Information signals can be transmitted via UWB radio in real-time for maintaining the neural spike sequence. For example, if 50 channels are monitored, each time a spike is detected on a channel, a number identifying the channel or origin of the neural spike is transmitted via UWB radio. Transmission can include a short delay due to processing. An indication of the channel or origin of the neural spike is transmitted via a short identification transmission. Short identification transmission resolves situations in which two or more neurons fire at the same time. For example, if identification requires 200 nanoseconds and a neural spike lasts 2 milliseconds (ms), the system has the capacity for transmitting the identification of 10,000 neural spikes. In a neural signal system having time designated to the nearest millisecond, the system can transmit identification for 5,000 neural spikes per millisecond.

The method of encoding spikes for radio transmission requires minimal power because the temporal firing patterns are simply reproduced by the radio transmission and the time of firing is inherent within the transmission structure. Thus, information regarding the time of a neural spike is not required, only a neural channel or origin identifier. This type of coding reduces the required bandwidth and reduces power consumption by more than 50%. Power consumption is further reduced because information is transmitted only when a neural spike is detected and the time required to transmit that information is very short compared to the intervals between neural spikes on a given channel. For example, if it takes 200 nanoseconds to transmit an information signal indicating a neural spike, a typical 50 Hertz firing rate for a given neuron would result in a duty cycle of only approximately 0.001 per channel, assuming one neuron per channel. All analog signal processing and spike sorting is performed prior to transmission on UWB transmitter.

As stated above, neural spike processor and transmitter 106 can include a memory for storing information signals. Data can be stored in terms of the time the neural spike was generated and/or the channel or location source of the neural spike. The memory can also receive and store the signal data with information identifying the sensory or motor activity ongoing at the time of the neural spike. Preferably, the memory stores the signals in a digital format. Alternatively, signal data can be represented by analog voltage records of the complete signal, a time multiplexed analog signal, analog records of only the neural spikes and a time indicator identifying the time of the neural spike, or any other suitable format known to those of skill in the art.

IV. Embodiments of a Neural Signal System

IV.A. Signal Receiver

Figure 4A:
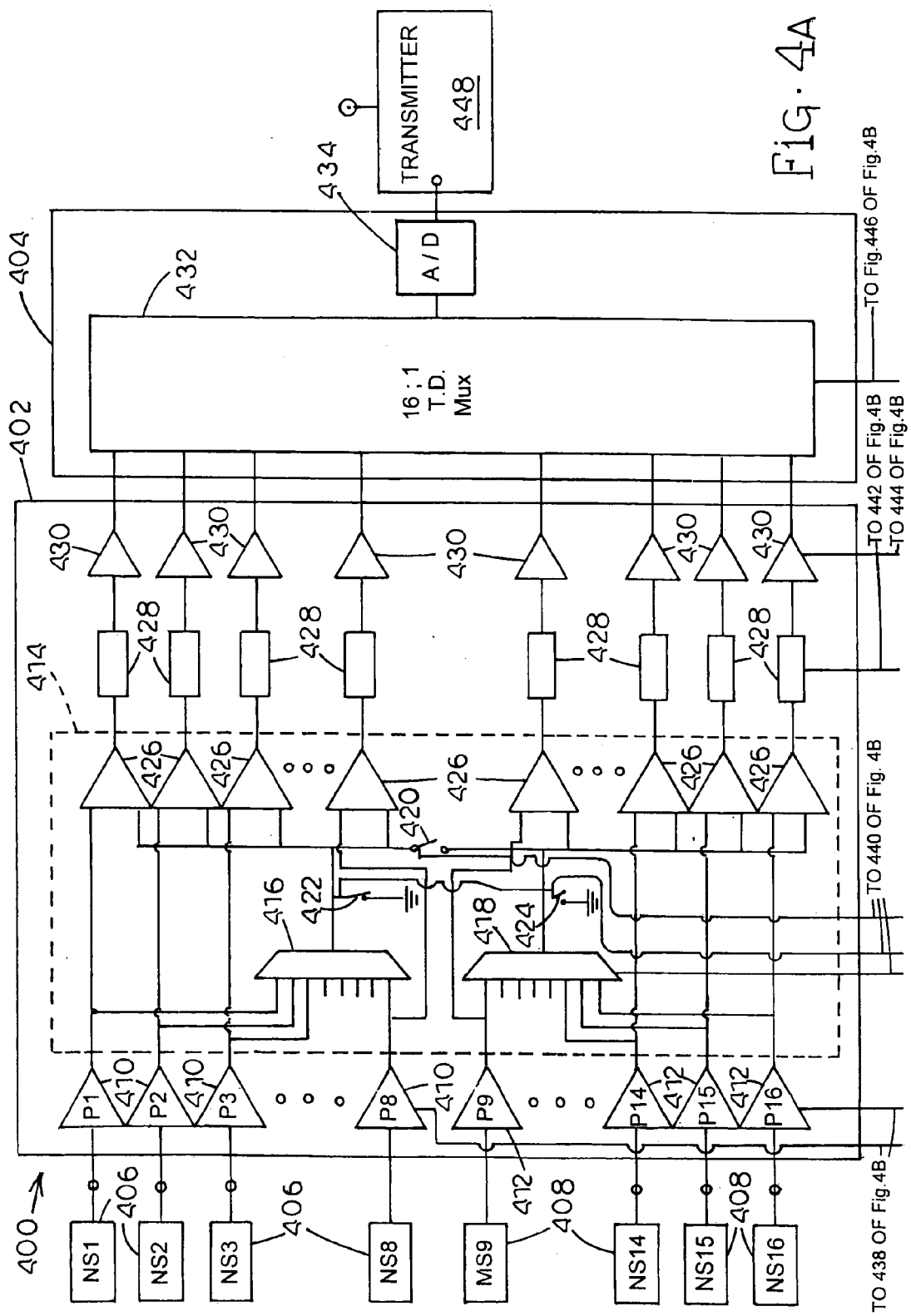
FIGS. 4A and 4B are a schematic views of a signal receiver having 16 channels according to an embodiment of the present invention.
Figure 4B:
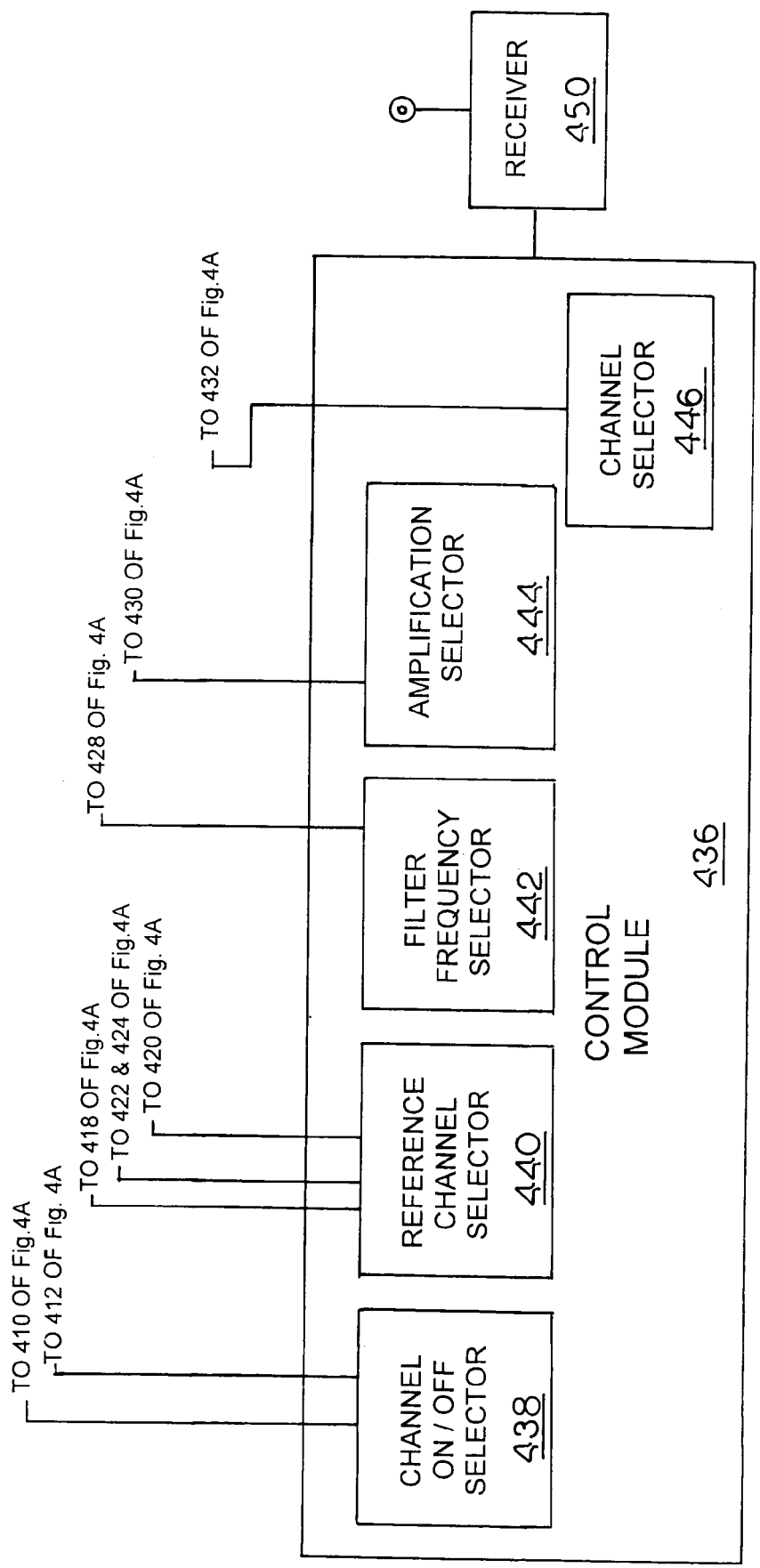

Referring to FIGS. 4A and 4B, schematic views of a signal receiver, generally designated 400, having 16 channels according to an embodiment of the present invention is illustrated. Signal receiver 400 can include a signal conditioner module 402 and an analog-to-digital (A/D) converter module 404. Signal receiver 400 is operable to receive neural signals from a first group of neural sensors 406 (NS1–NS8) and a second group of neural sensors 408 (NS9–NS16), condition the neural signals, and provide a digital representation of the neural signals to a neural spike detector or other hardware and/or software combination for further processing such as neural spike detection, sorting, display, or control of a prosthetic device. Signal conditioner module 402 can include input channels for receiving neural signals and connecting first and second group of neural sensors 406 and 408 to a first group of preamplifiers 410 (P1–P8) and a second group of pre-amplifiers 412 (P9–P16), respectively, for providing high gain input amplification and band pass filtering for the neural signals of first and second group of neural sensors 406 and 408, respectively. Preamplifiers 410 and 412 can be followed by a differential amplifier module 414 having a first and second multiplexer 416 and 418 and switches (not shown) for selecting two neural sensors from first and second group of neural sensors 406 and 408, respectively, for providing reference signals to eliminate common mode noise, described in more detail below. Such signal could come from a standard neural sensor or from a sensor designed specifically to act as a reference electrode. Further, differential amplifier module 414 can include a switch 420 connected between the outputs of multiplexer 416 and 418 for selecting any of neural sensors 406 and 408 to provide a reference signal. Differential amplifier module 414 can also include switches 422 and 424 connected between the output of multiplexers 416 and 418, respectively, and ground for selectively grounding the reference signal from either multiplexer 416 or multiplexer 418. Differential amplifier module 414 can also include differential amplifiers 426 for providing a difference signal that between a neural signal and one of the reference signals for eliminating common mode noise signals. Differential amplifiers 426 can also provide additional gain to the neural signals. In one embodiment, multiplexers 416 and 418 comprise ANALOG DEVICES™ AD708 multiplexer produced by Analog Devices, Inc. of Norwood, Me. In one embodiment, switch 420, 422, and 424 is a MAXIM™ 4626 switch produced by Maxim Integrated Products, Inc. of Sunnyvale, Calif.

Signal conditioner module 402 can include filters 428, described in more detail below, connected to differential amplifiers 426 for providing high and low pass filtering to the difference signals. In one embodiment, filters 428 can be adjusted to filter different frequency ranges. Filters 428 can be followed by variable gain amplifier 430 for selectively adjusting the gain of the signals. In the case of analog-to-digital conversion in a later stage, the gain adjustment can reduce the number of bits of resolution required in the analog-to-digital converter.

Signal receiver 400 can also comprise a control module 436 for controlling various components of signal conditioner module 402 and A/D converter module 404. Control module 404 can be an autonomous system or an operator-assisted system. In the case of an operator-assisted system, the operator visualizes each signal in turn and decides if the signal is an appropriate neural signal or is noise and turns the channel on or off depending on this decision. The operator can select the appropriate reference electrode by looking for one channel that shows little or no discrete activity and would thus be suitable as a reference. Similarly, the operator can optimize the gain on a particular channel based on the size of the neural signals. In the case of an autonomous or semi-autonomous system, a computer program can search for similar criterion as described above for selecting the proper control settings. For instance, the rate of neural spiking as determined by the detector can be an indication if the signal had an appropriate neural signal or was just measuring noise. For automatic gain selection, an autonomous device can monitor the signal levels and adjust the gain so that the fall within a specific voltage range suitable for processing by the A/D converter or other following stage. Control module 404 can receive signals from a processor (not shown) for controlling the components of signal conditioner module 402 and A/D converter module 404. Control module 404 can be implanted into a subject or worn by the subject.

Control module 402 can comprise a channel on/off module 438 connected to preamplifiers 410 and 412 for selectively powering preamplifiers 410 and 412. Module 438 can turn on/off each preamplifier of preamplifiers 410 and 412 for conserving power when it is determined that a corresponding one of neural sensors 406 and 408 is receiving a suitable neural signal from the subject. Selector 438 is shown in FIGS. 4A and 4B connected to only one of preamplifiers 410 and 412 for clarifying the illustration.

Control module 436 can comprise a reference channel selector 440 connected to multiplexers 416 and 418 and switches 420, 422, and 424 for choosing a neural signal or ground as a reference signal. Selector 440 can select one of the inputs into multiplexers 416 and 418 as an output to function as a reference signal. Additionally, selector 440 can control switches 422 and 424 to close to provide ground as a reference signal or open to provide for the output of multiplexers 416 and 418 as the reference signal. Switch 420 can be controlled to select any of neural sensors 406 and 408 as a reference signal as described above.

Control module 436 can comprise a filter frequency selector 442 connected to filters 428 for selectively adjusting the frequency ranges filtered by filters 428. The frequency ranges can be selected by adjusting either the capacitive or resistive components of filters 428. The capacitive elements could be adjusted using electronic switches to add or delete discrete values of capacitance. The resistive components of the filter circuit can be adjusted using a digital potentiometer or another suitable adjustable resistive component known to those of skill in the art. If the filters 428 are composed of integrated switched capacitor elements, the frequency can be adjusted by modifying the clock frequency used to drive the switched capacitor elements. Selector 442 is shown in FIGS. 4A and 4B connected to only one of filters 428 for clarifying the illustration.

Control module 436 can comprise an amplification selector 444 connected to amplifiers 430 for selecting a magnitude of amplification for each of amplifiers 430. The amplification can be adjusted by modifying the resistive elements of the amplifier circuit or in the case of a switched capacitor amplifier by adjusting the clock frequencies. Selector 444 is shown in FIGS. 4A and 4B connected to only one of amplifiers 410 and 412 for clarifying the illustration.

Control module 436 can comprise a channel selector 446 connected to multiplexer 432 for selecting the channels output to A/D converter 434. Multiplexer 432 can control multiplexer 432 to output only the channels carrying suitable neural signals.

Figure 5:
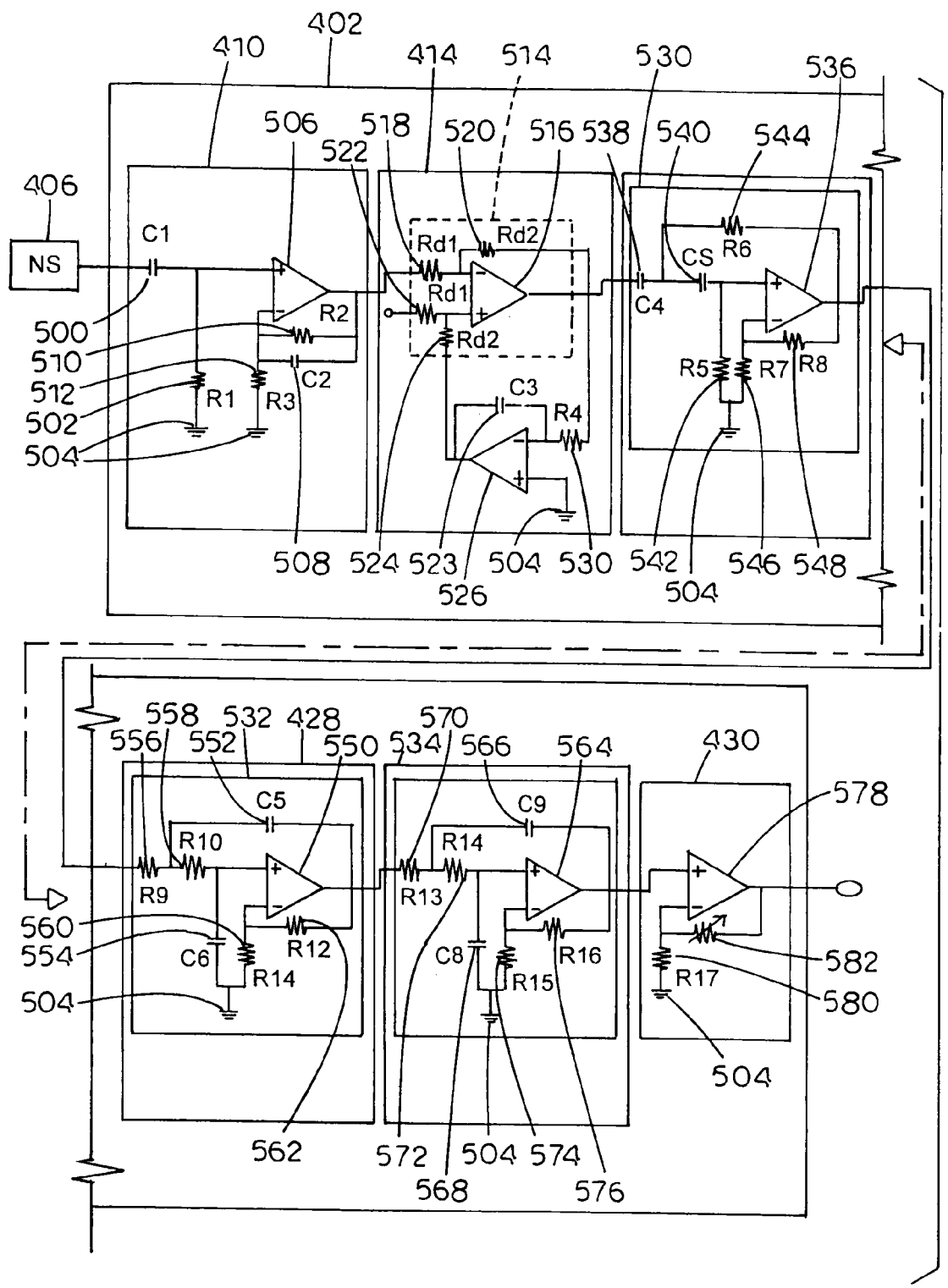
FIG. 5 is a schematic view of a signal conditioner module following a neural sensor according to an embodiment of the present invention.

Referring to FIG. 5, a schematic view of components in signal conditioner module 402 following a neural sensor 406 according to an embodiment of the present invention is illustrated. Signal receiver 400 can be include a gain to vary between 3,200 and 50,000. Signal receiver 400 can also have bandpass filter corner frequencies of about 350 hertz and 8,000 hertz. Small amplitude noise signals detected by neural sensors 406 and 408 necessitate low noise and high gain preamplifiers 410 and 412. Noise can be limited by combining a low noise operational amplifier and a low-pass filter. Preamplifier 410 can include a capacitor C1 500 and a resistor R1 502 connected to neural sensor 406 and ground 504 for providing a unity gain, high-pass filter. The output of the unity gain, high-pass filter is followed by a non-inverting, low-pass filter having gain. The high-pass filter can include an operational amplifier 506, a capacitor C2 508, and resistors R2 510 and R3 512. The output of the low-pass filter can be connected to the non-inverting input of operational amplifier 506 to prevent loading of the high-pass filter. Resistor R2 510 and capacitor C2 508 are connected in a feedback configuration from the output of to the inverting input of operational amplifier 506. Resistor R3 512 is connected between ground 504 and the inverting input of operational amplifier 506. In one embodiment, operational amplifier 506 is a MAXIM™ 4253 operational amplifier produced by Maxim Integrated Products, Inc. of Sunnyvale, Calif. for featuring low noise and shutdown to reduce power consumption when not operational. In this embodiment, the gain of preamplifier 410 is 100.

As stated above, differential amplifier module 414 can follow preamplifiers 410 and 412. Differential amplifier module 414 follows preamplifiers 410 and 412 for applying more gain in an early stage and improving signal quality by allowing for the rejection of common-mode noise signals. Module 414 can include a differential amplifier 514 (indicated with broken line). In this embodiment, differential amplifier 514 is a MAXIM 4199 differential amplifier produced by Maxim Integrated Products, Inc. of Sunnyvale, Calif. for providing a differential gain with a common mode rejection ratio (CMRR) of about 110 decibels. Differential amplifier 514 can include an operational amplifier 516, resistors Rd1 518 and Rd2 520 of the inverting input and resistors Rd1 522 and Rd2 524 of the noninverting input. The output of preamplifier 410 is connected to resistor Rd1 518 of differential amplifier 514. The reference signal selected by multiplexers 416 and 418 (shown in FIGS. 4A and 4B) is connected to the resistor Rd1 522 of differential amplifier 514. Module 414 can also include an operational amplifier 526, a capacitor C3 528, and a resistor R4 530 configured as an integrator in the feedback of differential amplifier 514. The noninverting input of operational amplifier 526 is connected to ground 504. Resistor R4 530 is connected between the inverting input of operational amplifier 526 and resistor Rd2 520 of differential amplifier 514. Capacitor C3 528 is connected between the inverting input of operational amplifier 526 and resistor Rd2 524 of differential amplifier 514. Placement of the integrator in the feedback path of differential amplifier 514 improves the common mode range by adding a high-pass pole to attenuate low frequency offset voltages. In one embodiment, operational amplifier 526 is Burr Brown OPA2244 operational amplifier produced by Texas Instruments Incorporated.

In one embodiment, filter 428 is configured with Bessel filters. Bessel filters can preserve the activation signals if any waveform-based spike sorter is used. Filter 428 can include one or more cascaded filters: (1) a high-pass filter 530, (2) a first low-pass filter 532, and (3) a second low-pass filter 534. Low pass filter 530 can include an operational amplifier 536, capacitors C4 538 and C5 540, and resistors R5 542, R6 544, R7 546, and R8 548. Capacitors C4 538 and C5 540 are connected in series between the noninverting input of operational amplifier 536 and the output of operational amplifier 516 of differential amplifier module 414. Resistor R6 544 is connected from the output of operational amplifier 536 to the node connecting capacitor C4 538 and C5 540. Resistor R5 542 is connected between ground 504 and the noninverting input of operational amplifier 536. Resistor R7 546 is connected between ground 504 and the inverting input of operational amplifier 536. Resistor R8 548 is connected between the output and the inverting input of operational amplifier 536.

First low-pass filter 532 can include an operational amplifier 550, capacitors C5 552 and C6 554, and resistors R9 556, R10 558, R1 560, and R12 562. Resistors R9 556 and R10 558 are connected in series between the noninverting input of operational amplifier 550 and the output of operational amplifier 536 of high-pass filter 530. Capacitor C5 552 is connected from the output of operational amplifier 550 to the node connecting resistors R9 556 and R10 558. Capacitor C6 554 is connected between ground 504 and the noninverting input of operational amplifier 550. Resistor R11 546 is connected between ground 504 and the inverting input of operational amplifier 550. Resistor R12 562 is connected between the output and the inverting input of operational amplifier 550.

Second low-pass filter 534 can include an operational amplifier 564, capacitors C7 566 and C8 568, and resistors R13 570, R14 572, R15 574, and R16 576. Resistors R13 570 and R14 572 are connected in series between the noninverting input of operational amplifier 564 and the output of operational amplifier 550 of first low-pass filter 532. Capacitor C7 566 is connected from the output of operational amplifier 564 to the node connecting resistors R13 570 and R14 572. Capacitor C8 568 is connected between ground 504 and the noninverting input of operational amplifier 564. Resistor R15 574 is connected between ground 504 and the inverting input of operational amplifier 564. Resistor R16 576 is connected between the output and the inverting input of operational amplifier 564.

Figure 6A:
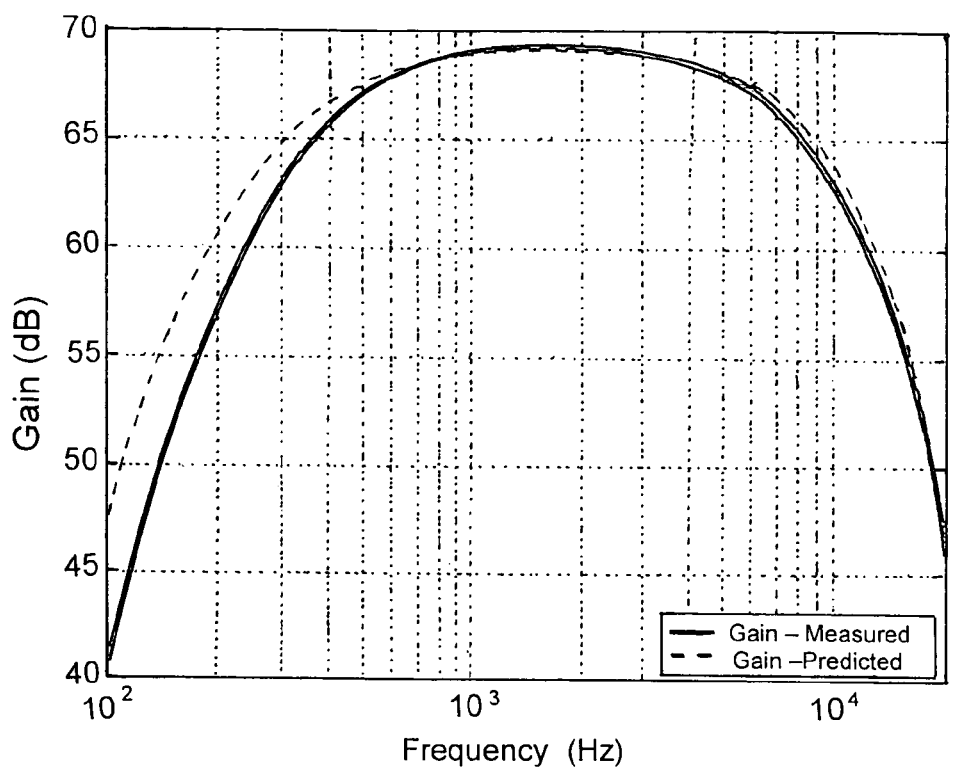
FIGS. 6A and 6B are graphical views of actual and measured phase and gain responses of the embodiment of the present invention described with regard to FIG. 5.
Figure 6B:
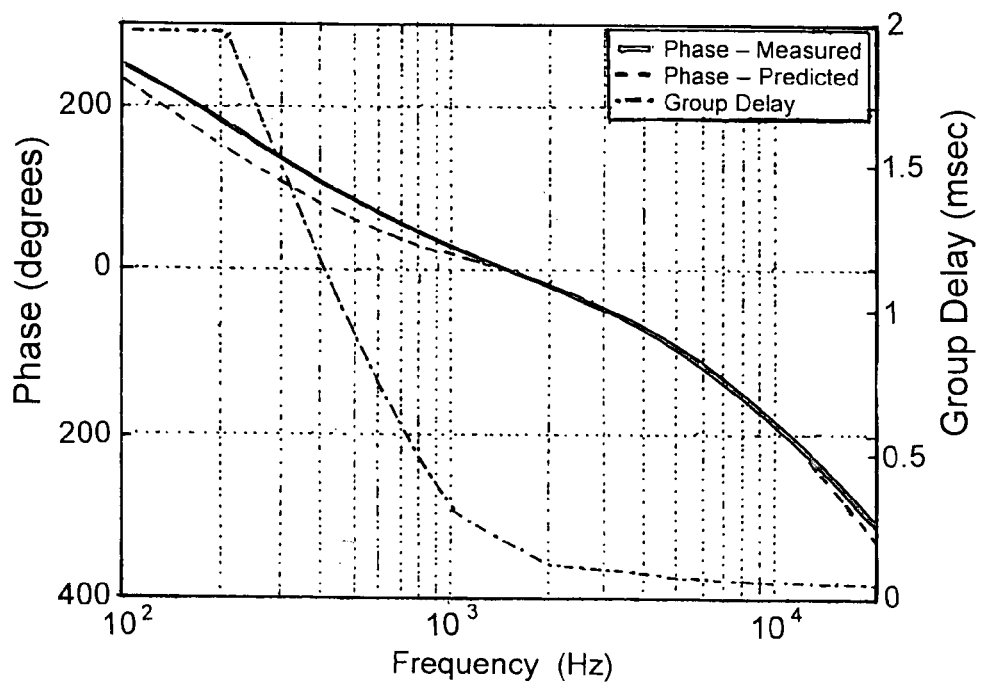

Since Bessel filters can tend minimize phase distortion at the expense of sharp filter roll-offs, higher order filters can be used. In the embodiment described with regard to FIG. 5, there are four high-pass and five low-pass poles. Referring to FIGS. 6A and 6B, graphical views of actual and measured phase and gain responses of the embodiment described with regard to FIG. 5. Referring specifically to FIG. 6A, the gain response in the vertical axis is shown verses the frequency spectrum in the horizontal axis. Referring specifically to FIG. 6B, the phase response in the left vertical axis and the group delay in the right vertical axis is shown verses the frequency spectrum in the horizontal axis. The maximum group delay at any frequency is about 2 milliseconds.

In one embodiment, high-pass filter 532, first low-pass filter 534, and second low-pass filter 536 can comprise three Sallen-Key filters for forming Bessel filters. The operational amplifiers in the three Sallen-Key filters can be a BURR-BROWN™ OPA4244 quad package produced by Texas Instruments Incorporated.

Variable gain amplifier 430 can be positioned after filters 428 for driving the capacitive input load of multiplexer 432. Variable gain amplifier 430 can include an operational amplifier 578, resistor R17 580, and a variable resistor 582. Variable gain amplifier 430 can increase the dynamic range of signal conditioner module 402. The output of operational amplifier 465 of second low-pass filter 534 can be connected to the noninverting input of operational amplifier 578. Resistor R17 580 can be connected between ground 504 and the inverting input of operational amplifier 578. Variable resistor VR 582 can be connected between the output and inverting input of operational amplifier 578 for controlling the gain of the input signal to variable gain amplifier 430. In one embodiment, variable resistor VR 582 is a 200 kiloohm potentiometer. Alternatively, variable resistor VR 582 can be a MAXIM™ 5160 potentiometer produced by Maxim Integrated Products, Inc. of Sunnyvale, Calif. The MAXIM™ 5160 is a 200 kiloohm, 32-tap digital potentiometer evenly spaced between one and 16.5. In one embodiment, operational amplifier 578 is available on the BURR-BROWN™ OPA4244 quad package for use in variable gain amplifier 430.

Referring again to FIGS. 4A and 4B, A/D converter module 404 can include a time-division multiplexer 432 and an A/D converter 434 for providing time-division multiplexing and sampling, respectively. Time-division multiplexer 432 can include 16 inputs for connection to the outputs of variable gain amplifiers 430. In one embodiment, time-division multiplexer 432 is an ANALOG DEVICES™ AD706 multiplexer produced by Analog Devices, Inc. of Norwood, Me. In one embodiment, A/D converter 434 includes 12-bit, low power, successive approximation analog-to-digital conversion with a maximum throughput rate of 1 mega samples per second for allowing each of the 16 channels to e sampled at up to 62.5 kilo samples per second. In one embodiment, A/D converter 434 is an ANALOG DEVICES™ AD7495 analog-to-digital converter produced by Analog Devices, Inc. of Norwood, Me. In one embodiment, timing signals for time-division multiplexer 432 and A/D converter 434 are produced on a separate integrated circuit board. The output of A/D converter 434 can be transmitted to a processor, such as a processor of computer system 902 shown in FIG. 9.

In one embodiment, signal conditioner module 402 and A/D converter module 404 are manufactured on the same integrated circuit board. Alternatively, signal conditioner module 402 and A/D converter module 404 can be manufactured on different boards. Power to signal conditioner module 402 and A/D converter module 404 can be supplied by voltage regulators (not shown). In one embodiment, the voltage regulators are two high precision, low dropout voltage regulators. The two voltage regulators can be ANALOG DEVICES™ REF191 and REF198 produced by Analog Devices, Inc. of Norwood, Me., which generate 2.048 volts and 4.096 volts, respectively. The 2.048 voltage rails of ANALOG DEVICES™ REF191 can be used as a virtual ground for effectively creating a ±2.048 volt power supply without requiring an inverting voltage regulator or negative power supply. Since the ANALOG DEVICES™ REF191, by acting as the virtual ground, is incapable of sinking current, its output can be buffered with a unity gain source follower, for example an ANALOG DEVICES™ OP262 produced by Analog Devices, Inc. The virtual ground can be used to ground the subject, provided that the power source is isolated from true ground.

In one embodiment, signal receiver 400 comprises a six-layer printed circuit board (PCB) for holding the components of signal receiver 400 and a power supply. The PCB can include two 30-pin digital input/output (I/O) connectors and a 20 pin analog input zero input force (ZIF) connector. The analog channels can be laid out in eight parallel rows on each side of a PCB. A high board density can be achieved by using the smallest available hand-solderable parts, such as size 0402 for the passive components, 6.25 mil trace widths, and 24 mil vias with 10 mil drill holes. The analog input connector can include the 16 input lines and two power lines and two ground lines for powering an active circuit. Preamplifiers 410 and 412 and differential amplifier module 414 can be protected from electromagnetic radiation by a grounded metal shield positioned over both sides of the PCB.

In one embodiment, a PCB having signal receiver 400 and a power supply includes 50 digital control signals listed in Table I below:

| Control Signal | Quantity |
| --- | --- |
| ADC Clock | 1 |
| ADC Chip Select | 1 |
| Variable Gain Up/Down | 1 |
| Ground Select Switches | 3 |
| Multiplexer 416 Sel/Enb | 4 |
| Multiplexer 418 Sel/Enb | 4 |
| Multiplexer 432 Sel/Enb | 4 |
| Channel Enable | 16 |
| Variable Gain Clocks | 16 |

The ADC clock and chip select control signals can control A/D converter 434. Variable gain up/down control signal can control the resistance of variable resistor VR 582 for adjusting the gain of variable gain amplifier 430. Ground select switches control signals can control switches 420, 422, and 424. Multiplexer 416 sel/enb, multiplexer 418 sel/enb, and multiplexer 432 sel/enb control signals can control multiplexers 416, 418, and 420, respectively. Channel enable and variable gain clocks control signals can control amplifier enable signals and the variable gain amplifiers in each channel.

Digital input/output can be handled through two parallel 30-pin connectors. The connectors can have 50 control signals, four reference power supply lines, four ground lines, and the output of A/D converter 434. In one embodiment, the connectors can be connected to a remote computer or processor for controlling and receiving signals from signal receiver 400. A/D converter 434 can be connected to a transmitter 448, as described herein, for transmitting the output of converter 434 to the remote computer or processor. Similarly, a remote transmitter can transmit control signals to a receiver 450 that are passed to control module 436 and used to set the state of selectors 438, 440, 442, 444, and 446.

Figure 7:
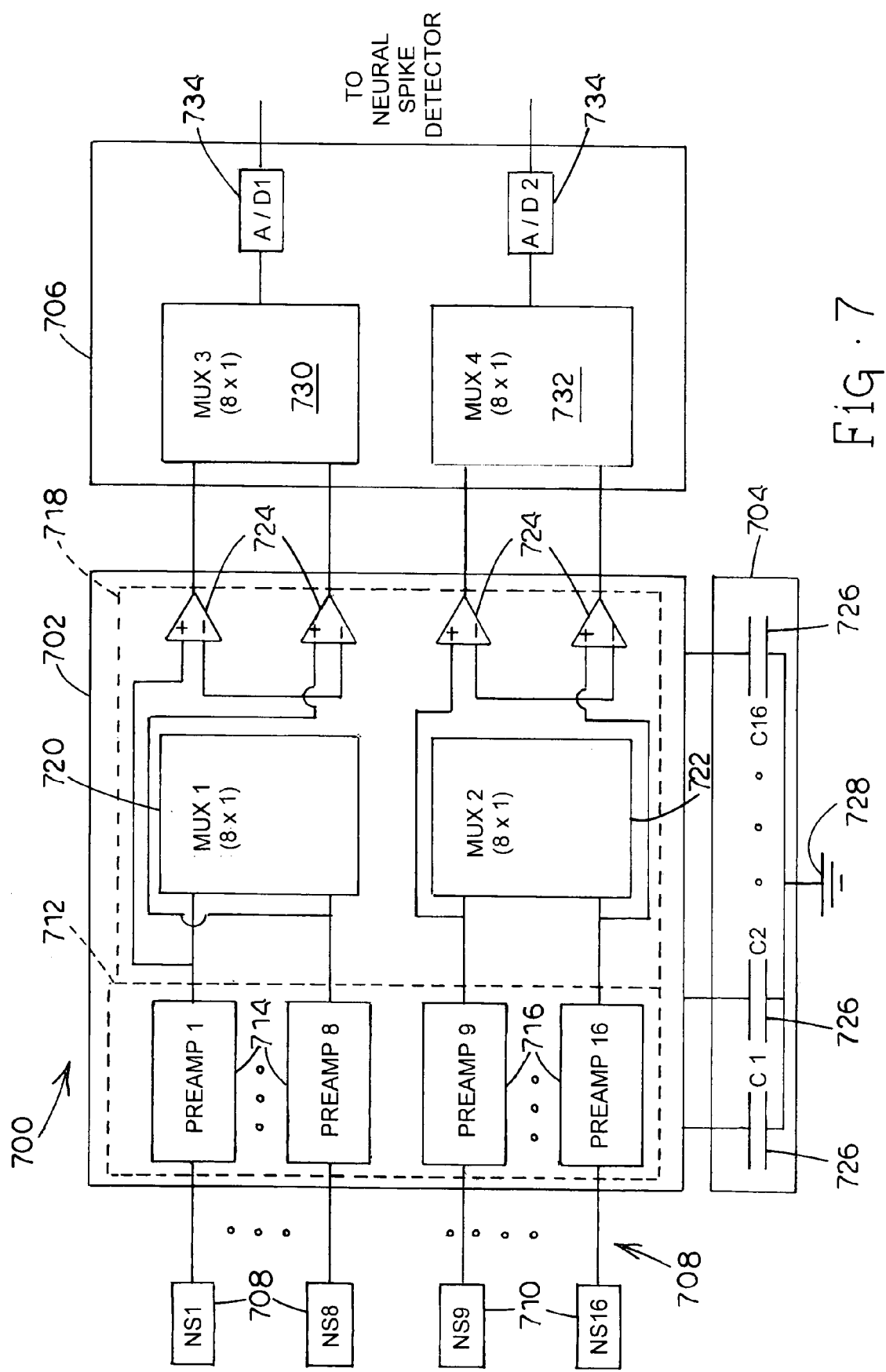
FIG. 7 is a schematic view of a signal receiver having 16 channels according to an embodiment of the present invention.

Referring to FIG. 7, a schematic view of a signal receiver, generally designated 700, having 16 channels according to another embodiment of the present invention is illustrated. Signal receiver 700 can include a signal conditioner module 702, a capacitor module 704, and an A/D converter module 706. Signal receiver 700 is operable to receive neural signals from a first group 10 of neural sensors 708 (NS1–NS8) and a second group of neural sensors 710 (NS9–NS16), condition the neural signals, and provide a digital representation of the neural signals to a neural spike detector or other hardware and/or software combination for further processing such as neural spike detection, sorting, display, or control of a prosthetic device. Signal conditioner module 702 can include input channels for receiving neural signals and connecting first and second group of neural sensors 708 and 710 to a pre-amplification stage 712 (indicated with broken line) having a first group of preamplifiers 714 (PREAMP1–PREAMP8) and a second group of preamplifiers 716 (PREAMP9–PREAMP16) for providing high gain input amplification and band pass filtering for the neural signals of first and second group of neural sensors 408 and 410, respectively. Pre-amplification stage 712 can be followed by a differential amplifier stage 718 (indicated with broken line) having a first and second multiplexer 720 and 722 for selecting two neural sensors from first and second group of neural signals 708 and 710, respectively, for providing reference signals to eliminate common mode noise, described in more detail below. Differential amplifier stage 718 can also include operational amplifiers 724 for providing a difference signal between a neural signal and one of the reference signals for eliminating common mode noise signals. Capacitor module 704 can include 16 capacitors 726 connected between a ground 728 and preamplifiers 714 and 716 for reducing the effect of DC offset.

Figure 8:
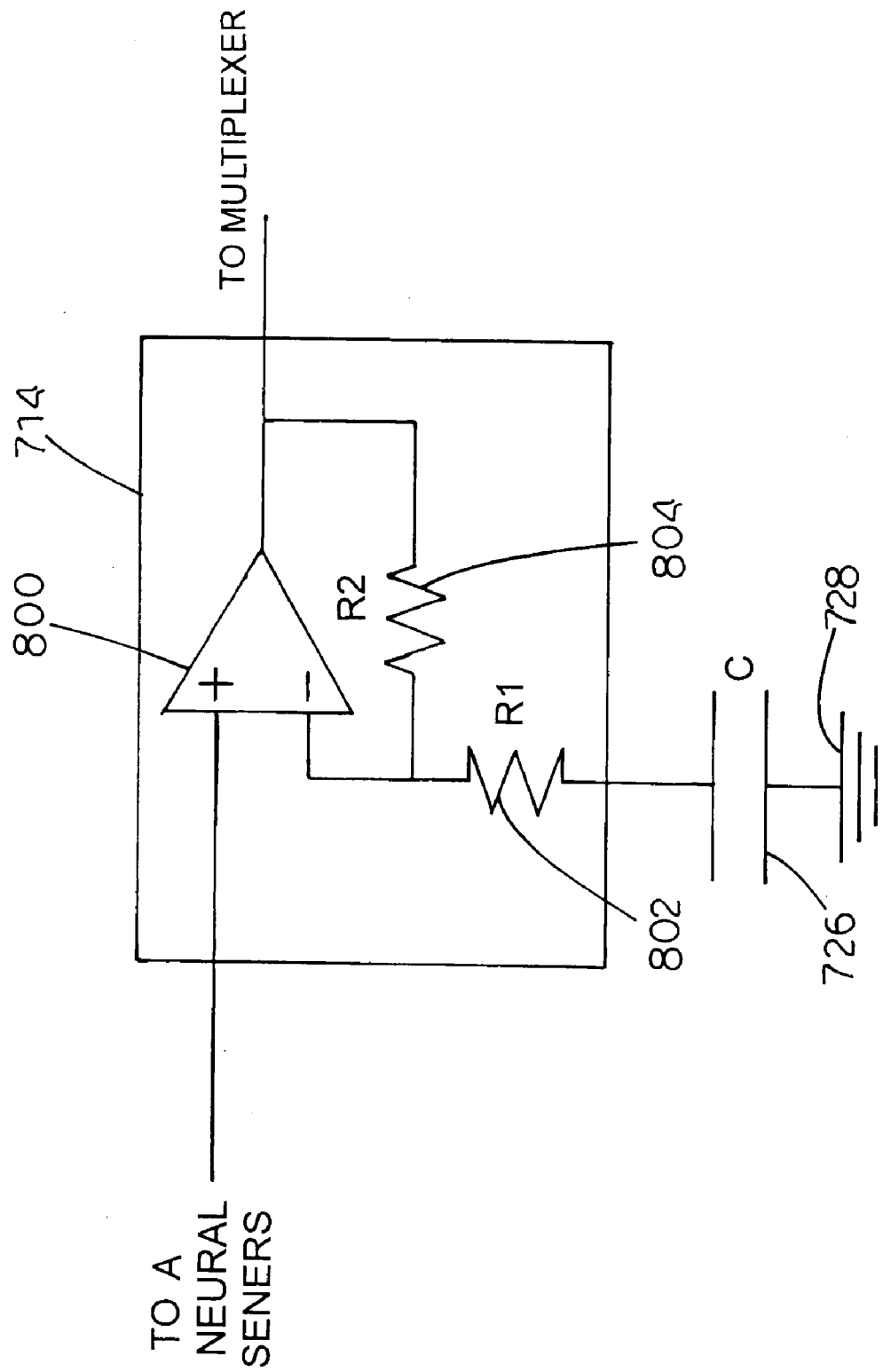
FIG. 8 is a schematic view of a preamplifier of signal conditioner module configured with an associated capacitor of a capacitor module according to an embodiment of the present invention.

Referring to FIG. 8, a schematic view of a preamplifier 714 of signal conditioner module 702 configured with an associated capacitor 726 of capacitor module 704 (shown in FIG. 7) according to an embodiment of the present invention is illustrated. Components of first group of preamplifiers 714 and second group of preamplifiers 716 are the same in this embodiment. As stated above, each preamplifier 714 is connected to one of capacitors 726 of capacitor module 704. Preamplifier 714 can include an operational amplifier 800 and resistors R1 802 and R2 804. Resistor R1 802 is connected between the inverting input of operational amplifier 800 and ground 728. Resistor R2 804 is connected between the output and inverting input of operational amplifier 800. In one embodiment, the configuration of operational amplifier 800 and resistors R1 802 and R2 804 provide a gain of 50. According to one embodiment, resistor R1 802 is 7.3 kilo ohms and R2 804 is 357 kilo ohms. Capacitor 726 is connected in the feedback of operational amplifier 800 between resistor R1 802 and ground 728 to provide a high-pass portion for forcing the gain of pre-amplification stage 712 to unity for DC signals. According to one embodiment, capacitor 726 is 100 nanofarads. The low-pass filter is provided by the gain bandwidth product of operational amplifier 800. Capacitor 726 provides correction of the DC offset problem associated with conditioning neural signals. Input from the neural signal can be connected to the noninverting input of operational amplifier 800. In this embodiment, pre-amplifier 714 provides a gain of 50 and band pass filtering between 218 hertz and 10,000 hertz to the received neural signal.

Preferably, signal conditioner module 702, capacitor module 704, and A/D converter module 706 are manufactured on separate integrated circuits. This design for pre-amplifier 714 has the advantage of high input impedance and large pass band gain and only one off chip component, capacitor 726, for signal conditioning and only one additional input/output (I/O) pin required to connect capacitor 726 to a preamplifier of first group of preamplifiers 714 or second group of preamplifiers 716. The circuit operation offers the advantage of reducing the effect of DC offset on a very broad range of neural sensors. This configuration can present a very high input impedance to the sensor thus allowing sensors with a high or low output impedance to be monitored. Manufacturing the modules on separate chips can allow commercial devices to be used for the capacitor module and the A/D converter modules. These parts can be made from different IC technologies and manufacturing them on different chips can allow the optimum technology to be used for each module.

Referring again to FIG. 7, as stated above, differential amplifier stage 718 can also include first and second multiplexers 720 and 722 for providing selection of a neural signal from a first group of preamplifiers 714 (PREAMP1–PREAMP8) and a second group of preamplifiers 716 (PREAMP9–PREAMP16) as reference signals to eliminate common mode noise. As stated above, signal receiver 700 can include inputs for 16 neural sensors 708, NS1 to NS16. In this embodiment, the neural sensors are divided into a first group (NS1–NS8) 708 and a second group (NS9–NS16) 710 for positioning in generally different locations of the neural tissue of a subject. First group (NS1–NS8) 708 and second group (NS9–NS16) 710 can be connected to first multiplexer 720 and second multiplexer 722, respectively, for selectively setting a reference signal for the neural signals of the respective group. Taking a reference signal from the portion of neural tissue close to the other sensors allows for the optimal cancellation of signals common to both sensors. These common signals are typically noise from both intrinsic and extrinsic sources. First multiplexer 720 and second multiplexer 722 include 8 inputs for connection to the outputs of first and second preamplifiers 714 and 716, respectively, and can be set to one of the neural signals of the respective group as the reference signal for output. Preferably, the reference signal is set to a suitable neural signal. A reference signal can contain all of the noise signals common to the neural signal but does not contain the neural signal itself. Thus, when the reference signal is subtracted from signal recorded from the neural electrode, all of the noise will be removed. A good reference signal can be purposely created by implanting a sensor specifically to be used as a reference sensor, or a reference signal can be selected from among the available neural signals by examining the signal properties of each one using a distant reference signal and determining which of the neural signals is composed of only noise signals and contains little or no components from discrete neural generators. In the alternative, signal receiver 700 can include circuitry for automatically selecting and setting suitable reference signals. The output of first multiplexer 720 and second multiplexer 722 can be connected to the inverting input of each of operational amplifiers 724 in its associated group of operational amplifiers. The outputs of preamplifiers 714 and 716 can be connected to one of the noninverting inputs of its associated operational amplifiers 724. Therefore, the resulting output of operational amplifiers 724 is the difference signal of the inputs. The difference signal is the difference between the input neural signal from one of preamplifiers 714 and 716 and the reference signal of one of multiplexers 720 and 722. Operational amplifiers 724 can also provide a gain to the difference signal. In one embodiment, operational amplifiers 724 provide a gain of 10.

A/D converter module 706 can include a third and fourth multiplexer 730 and 732 for multiplexing the difference signals at the outputs of operational amplifiers 724 into two signals for analog-to-digital conversion by A/D converters 734. The outputs of A/D converters 734 is the digital representation of the difference signal. Alternatively, module 706 can include a number of multiplexers up to one half of the total number of channels and a number of A/D converters 734 up to the total number of channels. The output of A/D converters 734 can be connected to a neural spike detector or other suitable hardware and/or software configuration, such as a computer system, for further processing.

Figure 9:
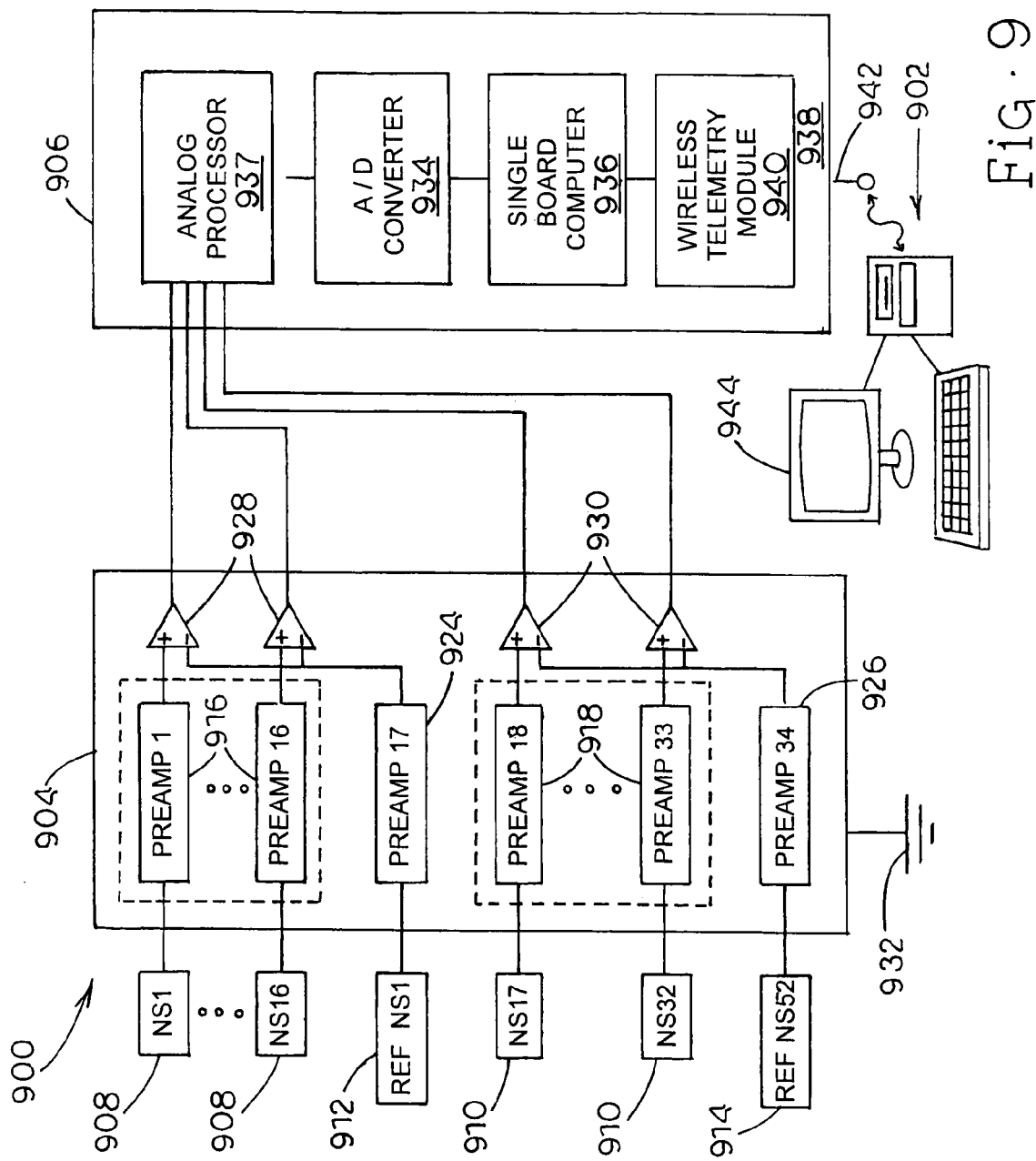
FIG. 9 is schematic view of a signal receiver having 32 channels and communication with a remote computer system according to an embodiment of the present invention.

Referring to FIG. 9, a schematic view of a signal receiver, generally designated 900, having 32 channels and communication with a remote computer system, generally designated 902, according to another embodiment of the present invention is illustrated. Signal receiver 900 can include a headstage component 904 attached to the outside of the skin of the head of a subject for receiving and conditioning neural signals from the subject. Further, signal receiver 900 can include a wearable component 906 for attachment to the subject and for further processing neural signal, converting the signal to a digital representation, and transmitting the signal to remote computer system 902.

Headstage component 904 can be attached to a first group of neural sensors (NS1–NS16) 908 and a second group of neural sensors (NS17–NS32) 910 for receiving electrical-based neural signals from the subject. The first and second group of neural signals 908 and 910 are positioned in generally different portions of the neural tissue of the subject. Headstage component 904 can also be connected to a first reference neural signal (REF NS1) 912 and a second reference neural signal (REF NS2) 914 positioned generally in the same portion of the neural tissue as first and second group of neural sensors 908 and 910, respectively, for providing a reference signal for eliminating common mode noise.

Headstage component 904 can include a first group of preamplifiers (PREAMP1–PREAMP16) 916 and a second group of preamplifiers (PREAMP18–PREAMP33) 918 attached to first and second group of neural sensors 908 and 910, respectively, for filtering and amplifying the neural signals. Headstage component 906 can further include preamplifiers 920 and 922 attached to reference neural sensors 912 and 914, respectively, for filtering and amplifying the reference neural signals. The preamplifiers can include a circuit for removing the DC offset. If the DC offset correction is not included, the output signals can connect to an analog processor of the type shown in, for example, FIG. 5 which corrects the DC offset using capacitor C1 500 and resistor R1 502 (shown in FIG. 5).

Headstage component 904 can further include a first group of operational amplifiers 920 and a second group of operational amplifiers 922 for providing a difference signal of the neural signals and an associated reference neural signal to eliminate common mode noise. If operational amplifiers 922 are included, the outputs of preamplifiers 916 and 918 can be connected to one of the noninverting inputs of an associated operational amplifier of first group of operational amplifiers 920 and second group of operation amplifiers 922, respectively. The output of preamplifiers 924 and 926 can be connected to the inverting input of each of first group of operational amplifiers 920 and second group of operation amplifiers 922, respectively. Therefore, the resulting output of operational amplifiers 928 and 930 is the difference signal of the inputs, the neural signal and its associated reference signal. Operational amplifiers 928 and 930 can also provide a gain to the difference signal. Preferably, operational amplifiers 928 and 930 provide a gain of 10. If operational amplifiers 922 are not included, then the signal outputs from 916, 918, 924 and 926 can be input to an analog processor of the type shown, for example in FIG. 5.

Wearable component 906 includes an analog processor 932 for receiving and processing the signals from operational amplifiers 928 and 930. Analog processor 932 can condition and time-division multiplexes the neural signals. Wearable component 906 can also include an analog-to-digital (A/D) converter 934 for converting the signal into a digital representation of the neural signal for receipt by a single board computer 936. A/D converter 934 can digitize signals at 30 k samples/second per channel at eight, ten, or 12 bits of resolution. Fifty digital inputs can be used for controlling channel enables, variable gain amplifiers, and analog to digital conversion timing. A/D converter 934 can include a regulated power supply 938 and pack the digitized data. In this embodiment, power supply 938 is powered by a pair of rechargeable lithium-ion batteries. Computer 936 can format the data from the A/D converter into a format which is suitable for transmission over standard media for instance TCP/IP or UDP protocols for a wired or wireless network. Computer 936 can also format the data for a wired or wireless non-standard media connection such as a point-to-point wired or wireless connection. Further, computer 936 can perform data reduction schemes including spike based data reduction such as spike detection and transmission or spike sorting. Additionally, computer 936 can also perform other types of data compression encoding familiar to those skilled in the art such as run length encoding or MPEG type compression. A/D converter module 934 includes power regulation circuitry, complex programmable logic device (CPLD), and a first-in first-out (FIFO) memory. CPLD can generate both static and timing control signals. The static signals are specified by an operator (via the wearable computer) and loaded into registers in the CPLD. The registers automatically assert signals onto the A/D converter and receiver modules thus controlling the function of these components.

Computer 936 can also prepare the digital signal for transmission by a wireless telemetry module 940 to remote computer system 902. Wireless telemetry module 938 and antenna 940 can transmit a representation of the neural signal to remote computer system 902 for further processing. In this embodiment, wireless telemetry module 938 comprises an IEEE (Institute of Electrical and Electronics Engineers) 802.11b wireless ethernet card for transmitting a distance up to 9 meters. Alternatively, computer 936 and wireless telemetry unit 940 can be another suitable wireless technology such as 802.11a, 802.11g, a Bluetooth module, UWB radio or a commercial or other point-to-point wireless connection.

Remote computer system 902 can include a processor, memory, and a telemetry component for receiving and processing the transmitted signal from antenna 942. Computer system 902 can further process the signal and display the received neural signal and any results of processing the neural signal to an operator on a display 944. Computer system 902 can be a commercial system for processing and receiving neural signals such as the Plexon MAP processor (plexon is in Texas) or could be a commercial computer with software to process the neural signals. In either case, the signals can be spike sorted, and processed as previously described within and across signals to derive control commands from the neural signals.

Figure 10:
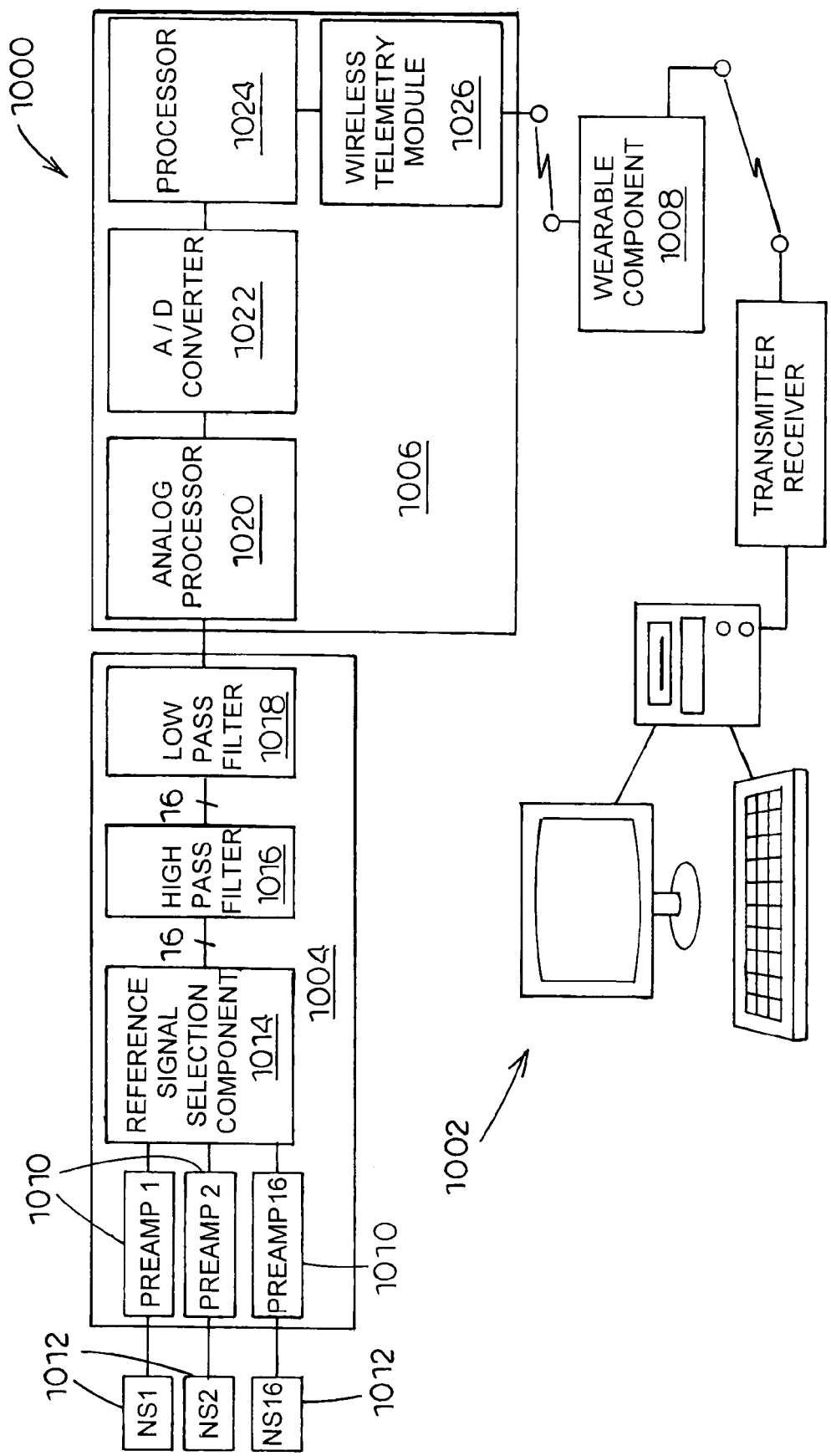
FIG. 10 is a schematic view of a signal receiver having 16 channels and communication with a remote computer system according to another embodiment of the present invention.

Referring to FIG. 10, a schematic view of a signal receiver, generally designated 1000, having 16 channels and communication with a remote computer system, generally designated 1002, according to another embodiment of the present invention is illustrated. In this embodiment, signal receiver 1000 is a headstage neurochip for implantation into a subject. Signal receiver 1000 can comprise a neural signal receiver 1004 and a neural signal processor and another implanted module 1006. Further, signal receiver 1000 can include a wearable component 1008 for attachment to the subject and for further processing neural signals, converting the signals to a digital representation, compressing the signals, and transmitting the signal to remote computer system 1002. Further, implanted module 1006 can communicate with wearable component 1008 using radio communication or optical communication. Wearable component 1008 can relay the control data from remote computer system 1002 or use software to determine the control settings. Wearable component 1008 can also relay a portion or all of the data from the implanted component to the remote computer system 1002. If only a portion of the data is relayed, this portion can be a compressed version of the signal or a processed version where the processing can be similar to that described above. The radio communication can be UWB radio, a commercial radio format such as 802.11a,b,g or other point-to-point radio technology. The optical communication can be near infrared light transmitted transcutaneously through the skin. The transmission can be analog or digital M-ary signals including binary. The transmission can be at other light wavelengths which are efficiently transmitted through the skin. Further, the transmission through the skin could be performed using acoustical energy in the form of analog or digital M-ary signals including binary. Such acoustical communication can be performed with a carrier frequency of between 1 and 50 Mhz or alternately using acoustical pulses of short duration encoding the information using pulse width, pulse position or pulse amplitude modulation.

Signal receiver 1004 can comprise preamplifiers (PREAMP1–PREAMP16) 1010 attached to neural sensors (NS1–NS16) 1012 for receiving electrical-based neural signals from the subject. Preamplifiers 1010 can filter and amplify the neural signals detected by neural sensors 1012.

Signal receiver 1004 can also comprise a reference signal selection component 1014 attached to preamplifiers 1010. Component 1014 can comprise multiplexers and/or differential amplifiers for selecting an appropriate reference signal. Signal receiver 1004 can also comprise a high pass filter 1016 and low pass filter 1018 for providing filtering to the neural signals. Filters 1016 and 1018 can pass all of the neural signal components (20–8000 Hz) or can pass a portion of the signal that allows for optimal spike detection and sorting.

Implanted module 1006 can include an analog processor 1020 for receiving and processing the signals from signal receiver 1004. Implanted module 1006 can also include an analog-to-digital (A/D) converter 1022 for converting the signal into a digital representation of the neural signal for receipt by a processor 1024. Processor 1024 can further process the digital signal by detecting or sorting spikes, processing spikes on a single channel by binning or some other integrating process, and combining information across neural signals to generate control signals. Processor 1024 can also prepare the digital signal for transmission as described herein by a wireless telemetry module 1026 to wearable component 1008. Wireless telemetry module 1026 can transmit a representation of the neural signal to remote computer system 1002 for further processing.

Wearable component 1008 can be worn directly over implanted component 1000 as would be suitable for optical or acoustic transmission. Additionally, wearable component 1008 can be worn directly over or nearby if radio transmission is used. According to one embodiment, wearable component 1008 can be positioned in a helmet worn over implanted module 1006. The components of implanted module 1006 can also be wired subcutaneously such that a transmitter can reside in another region of the body and the wearable component 1008 can be positioned over the transmitter in that region. According to one embodiment, several neural signal receiver modules can be placed near the electrodes and the transmitter placed subcutaneously near the pectoral region of the chest. These modules can be connected together using subcutaneous wires tunneled inside the body. The wearable relay system can be placed in a vest or jacket with telemetry module 1026 positioned over the implanted transmitter module.

Remote computer system 1002 can include a processor, memory, and a telemetry component for receiving and processing the transmitted signal from antenna 1028. Computer system 1002 can further process the signal as described herein and display the received neural signal and any results of processing the neural signal to an operator on a display 1030. Computer system 1002 can also process the signals as described above to derive control signals to control a prosthetic device or other devices as described above.

Figure 11:
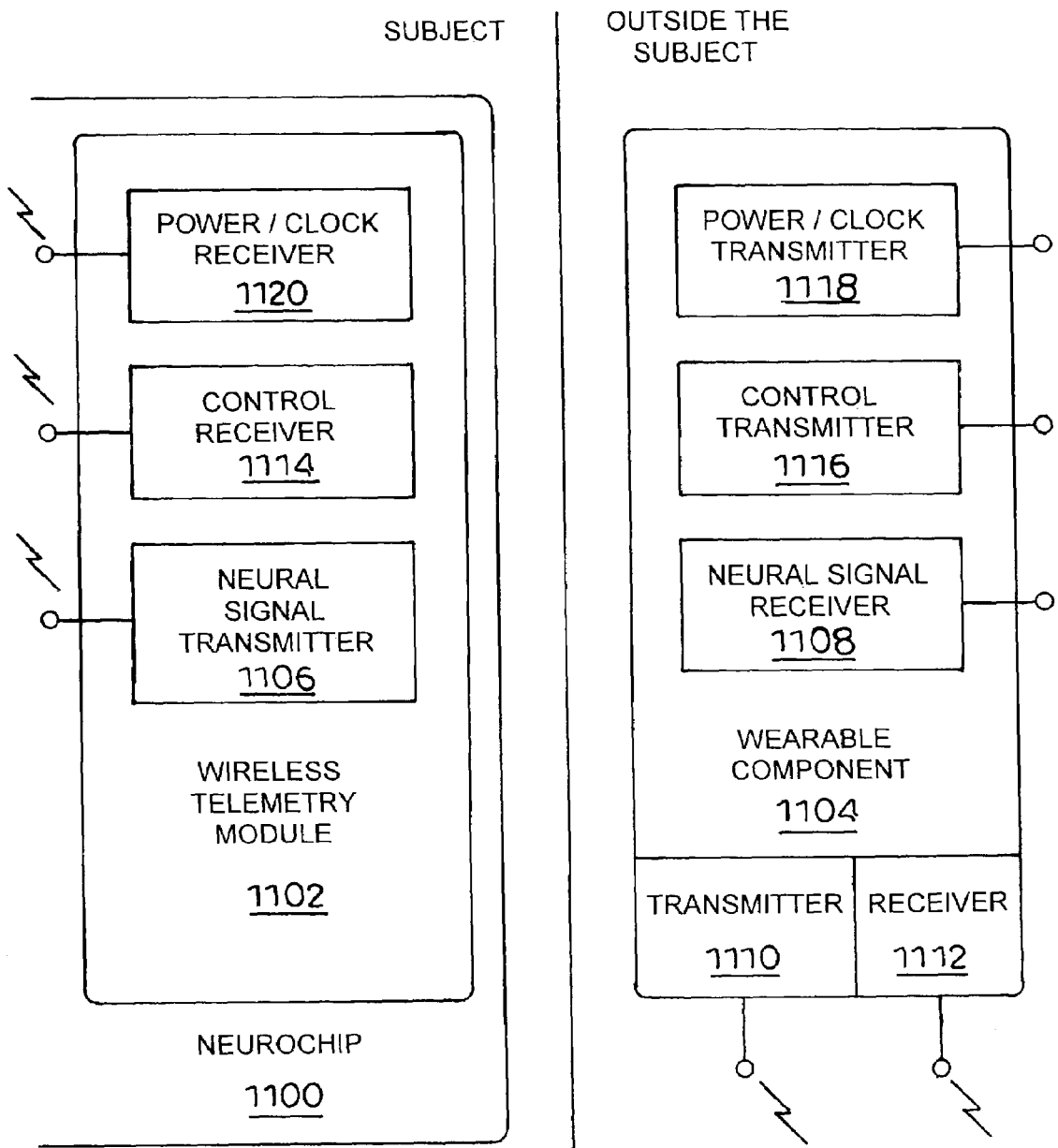
FIG. 11 is a schematic view of a neural spike detector according to one embodiment of the present invention.

Referring to FIG. 11, a schematic view of a neurochip 1100 including a wireless telemetry module 1102 implanted subcutaneously in communication with a wearable component 1102 positioned outside the skin and adjacent neurochip 1100. Wireless telemetry module 1102 can comprise a neural signal transmitter 1106 for transmitting conditioned neural signals. Wearable component 1104 can comprise a neural signal receiver 1108 for receiving the conditioned neural signals.

Wireless telemetry module 1102 and wearable component 1104 can communicate control signals to a control module, such as control module 436 shown in FIGS. 4A and 4B, for controlling various components of signal conditioner module, such as signal conditioner module 402 shown in FIGS. 4A and 4B, and an A/D converter module, such as converter module 404 shown in FIGS. 4A and 4B. Wearable component 1104 can transmit control signals to neurochip 1100 via a transmitter 1110. The control signals can originate from a processor in wearable component 1104 running an algorithm as described below, or can relay the control information from a remote processor under operator control or under the control of an algorithm. Wearable component 1104 can also receive data signals from neurochip 1100 via a transmitter 1112 and process or compress the data signals. Wearable component 1104 can also transmit the modified data to a remote receiver for further processing and for device control.

The control signals can be generated by a processor that examines the neural signals to determine the usefulness of a given signal. If a given signal is considered useful, for example because it contains characteristic spikes as determined by an operator or an algorithm, then the control signals which control the power to that channel are enabled and the control signals which control the multiplexer and A/D converter are enabled to sample and convert the given channel. Also, if a channel is enabled, the control signals controlling the amplification and filtering are manipulated to provide an optimized neural signal for later detection and sorting. For instance, the gain can be adjusted by an operator or an algorithm such that the amplitude of the largest spikes fill ⅔ of the A/D converter input range. Similarly, the filter setting can be optimized by an operator or an algorithm to give a characteristic neural waveshape. The control signals can be generated by an analog or digital processor that is located in neurochip 1100, located in the implanted signal processor, one of the wearable components or in the remote signal receiver. They could originate from a processor performing an algorithm as described, or could be controlled through the processor by an operator. Wireless telemetry module 1102 can comprise a control receiver 1114 for receiving the control signals. Wearable component 1104 can comprise a control transmitter 1116 for transmitting control signals to control receiver 1114.

Wearable component 1104 can subcutaneously transmit power to neurochip 1102. Wearable component 1104 can comprise a power/clock transmitter for transmitting power and a clock signal electromagnetically to wireless telemetry module 1102. Wireless telemetry module 1102 can comprise a power/clock receiver 1120 for receiving the power and clock signal from power/clock transmitter 1118. The clock signal can be important when there is more than one neural signal receiver, as spikes obtained from different anatomical locations need to be synchronized to a single clock source. The clock source can be generated by a processor or IC in wearable component 1104 or in a remote receiver.

IV.B. Neural Spike Detection

Figure 12:
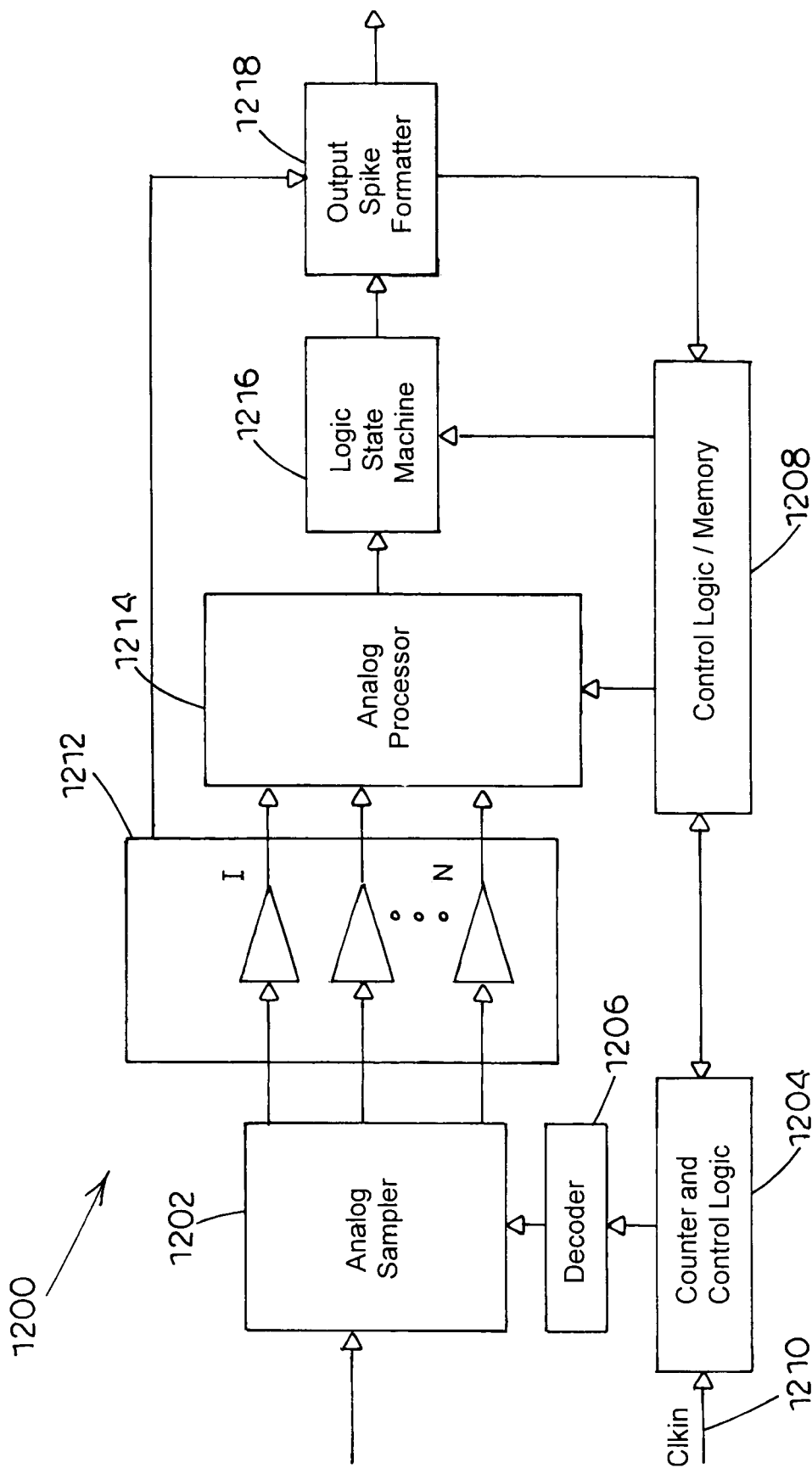
FIG. 12 is a schematic view of a neural spike detector according to one embodiment of the present invention.

Referring to FIG. 12, a schematic view of a neural spike detector, generally designated 1200, according to one embodiment of the present invention is illustrated. Neural spike detector 1200 can include an analog sampler 1202 for receiving the analog conditioned neural signals of a single neural sensor from a signal receiver. Analog sampler 1202 samples the conditioned signal N times and stores the N samples. Neural spike detector 1200 can include a counter and control logic module 1204, decoder 1206, and control logic/memory module 1208 for controlling sampling. Module 1204 can be operable to receive a clock signal input 1210 for synchronization with a signal receiver or neural spike processor. In one embodiment, the N samples are stored in analog form such as by a low leakage capacitor. Alternatively, the N samples can be stored in digital form. Neural spike detector 1200 can include a buffer array 1212 having N buffers for buffering and driving each of the N samples. Neural spike detector 1200 can also include an analog processor 1214 for receiving the N samples from buffer array 1212. In one embodiment, analog processor 1214 combines the N samples by implementing a scaling (gain) and summing algorithm. Alternatively, the N samples can be combined using gain and/or power operations known to those of skill in the art. Analog processor 1214 characterizes the results of the operations using a comparison to threshold levels in the processor and output to a logic state machine 1216. Logic state machine 1216 determines whether a neural spike has been detected. On the detection of a spike, the N samples in buffer array 1212 can be passed to an output spike formatter 1218 for transmission for further processing, such as spike sorting and interpretation. The output of output spike formatter 1218 is the N samples stored in buffer array 1212 and M samples that are immediately following the N samples. The M samples can be used for further characterizing the neural spike. In one embodiment, the sampling rate is 40 kHz, N is 8, and M is 32. Control logic/memory module 1108 can control operation of analog processor 1214 and logic state machine 1216.

Figure 13:
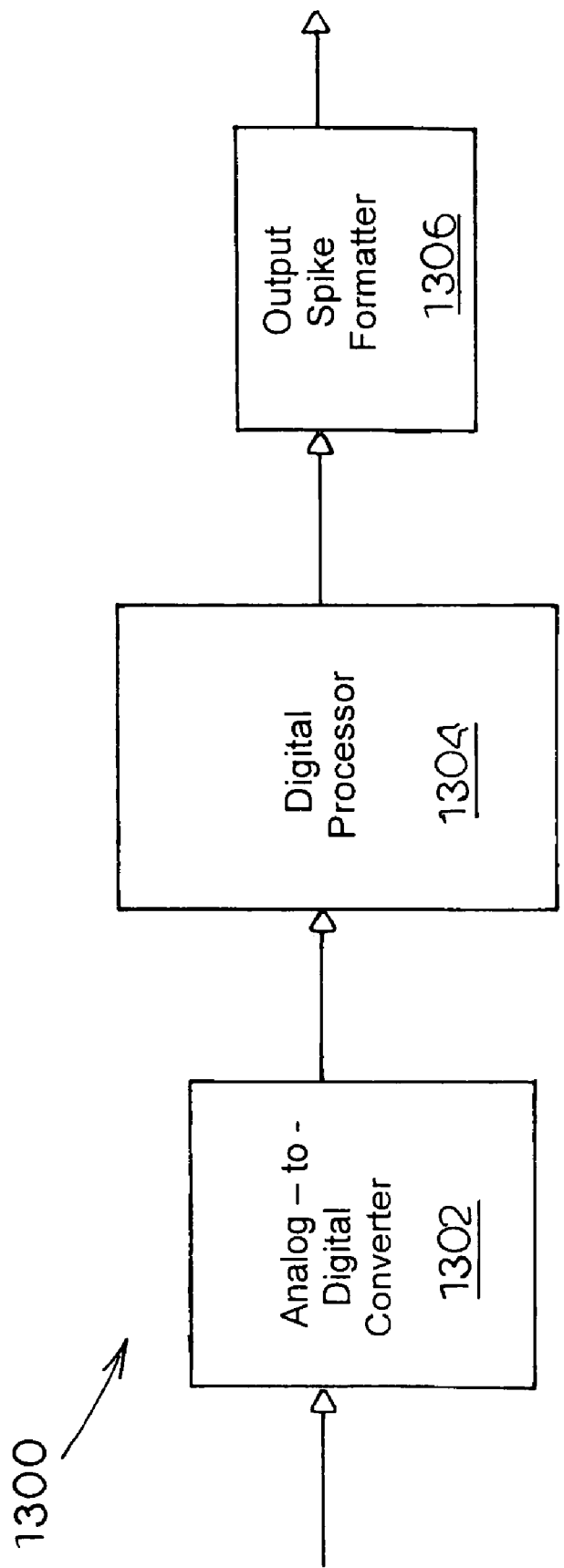
FIG. 13 is a schematic view of a signal transmitter according to an embodiment of the present invention.

Referring to FIG. 13, a schematic view of a neural spike detector, generally designated 1300, according to one embodiment of the present invention is illustrated. Neural spike detector 1300 can include an analog-to-digital converter 1302 for receiving the analog conditioned neural signals of a single neural sensor from a signal receiver. Analog-to-digital converter 1302 can convert the conditioned neural signal into a digital representation. Neural signal detector 1302 can also include a digital processor 1304 for detecting neural spikes in the neural signal. In one embodiment, neural spikes are detected by (1) sampling the conditioned signal; (2) combining the samples; (3) comparing the combined samples to predetermined thresholds; and (4) determining whether a spike has been detected based on the comparison in step (3). Digital processor 1304 can transmit samples of a neural spike to an output spike formatter 1306 for transmission to a device for further processing.

IV.C. Neural Spike Processor and Transmitter

Figure 14:
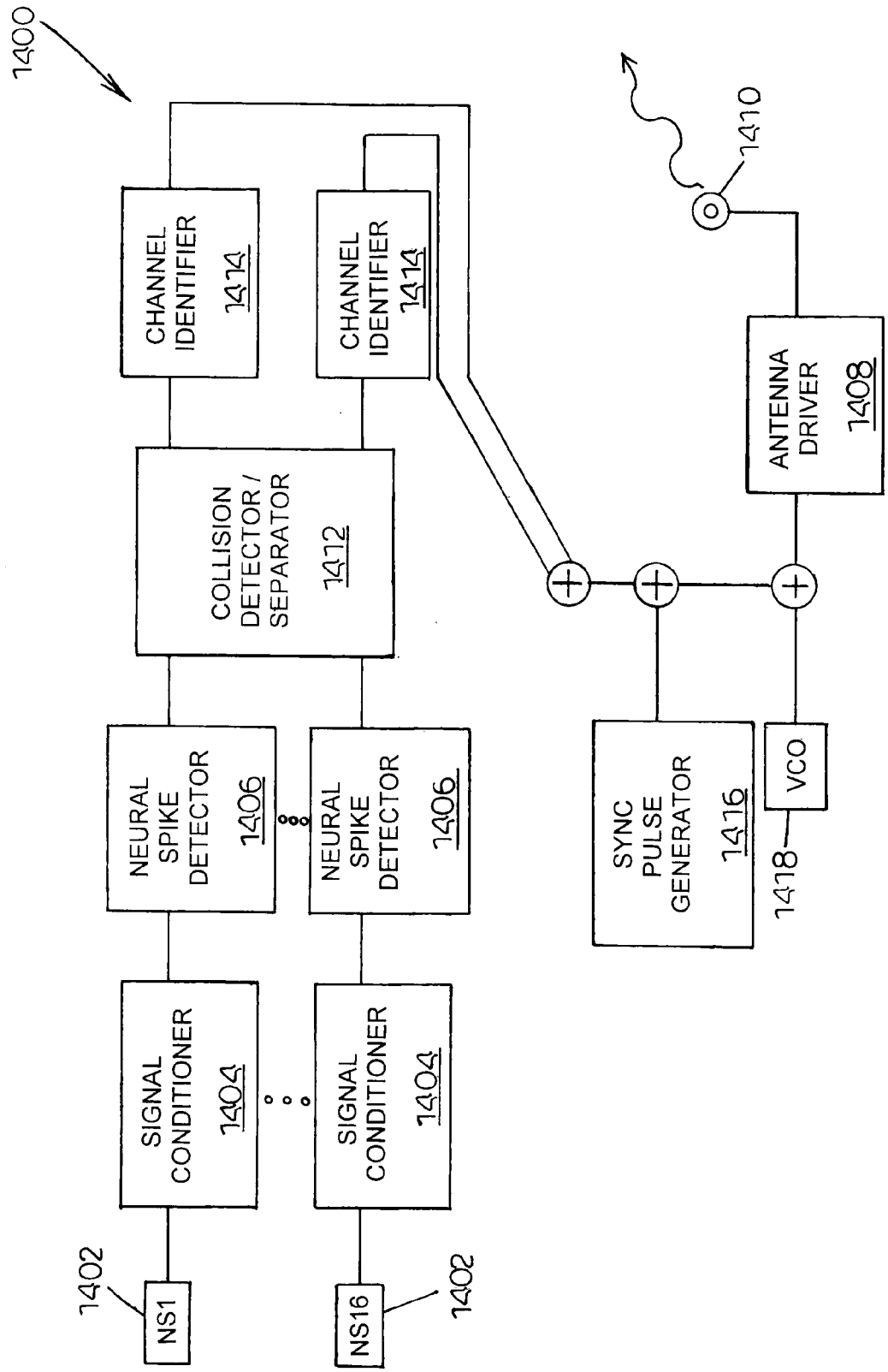
FIG. 14 is a schematic view of a signal receiver and a spike processor according to one embodiment of the present invention.

Referring to FIG. 14, a schematic view of a signal transmitter, generally designated 1400, according to an embodiment of the present invention is illustrated. Signal transmitter 1400 is advantageous because signal transmission includes UWB transmission, wherein data is transmitted only when a neuron spike is detected on any of the input neural signals from neural sensors (NS1–NS16) 1402. UWB transmission saves significant power consumption. Signal transmitter 1400 includes an asynchronous wideband protocol having channel identifiers and time stamp coding so that when a spike is detected on any one channel the time and source can be uniquely identified.

Signal transmitter 1400 can include signal conditioners 1404 and neural spike detectors 1406. Each neural sensor 1402 can be connected to one of signal conditioners 1404 for providing filtering and amplification to the detected neural signals. Signal conditioners 1404 can be connected to neural spike detectors 1406. Neural spike detectors 1406 are operable to detect a neural spike on the conditioned neural signal and transmit a pulse signal on the detection of a neural spike. Neural spike detectors 1406 can generate a UWB pulse sequence consisting of pulses of approximately one nanosecond in duration on the detection of a neural spike.

Generally spike signal trains have a repetition rate of between approximately 10 and 50 Hertz and spike duration of between approximately 1 and 2 milliseconds. Thus, there is significant dead time between the neural spikes allowing all of the spike information about one spike to be transmitted before another spike on the same channel occurs. The wide band nature of signal transmitter 1400 is generated from the very narrow (~1 nanosecond) digital pulse signals that are generated and transmitted to an antenna driver 1408 and antenna 1410.

Signal transmitter 1400 can include a collision detector and separator component 1412 for preventing any overlap of neural spike pulses occurring simultaneously from all of neural spike detectors 1406. On the detection of an overlap, component 1412 queues the pulses and transmit the pulses to channel identifiers 1414. Channel identifiers 1414 can replace each pulse with a generated channel identification code having m bits for indicating the origin neural sensor 1402. The channel identifier encoder that creates a unique digital code (m bits in length) for each channel is provided by the equation $2^m = n$.

The digital data generated by component 1412 is summed together and transmitted to a sync pulse generator 1416. Generator 1416 interleaves a period sync pulse with the data pulses. The sync pulse can keep the signal receiver, described below, and signal transmitter 1400 in synchronization. The sync and data pulses can then be convolved with the signal generated by a VCO 1418. The resulting signal is transmitted to antenna driver 1408 and antenna 1410 for transmission. The pulsewidth of the baseband signal determines how many VCO cycles will be transmitted per symbol. In this embodiment, each sync and data pulse is represented by half cycles of the VCO waveform, but can also be increased by integer multiples for improved symbol recover rate in the presence of noise within the signal receiver.

Figure 15:
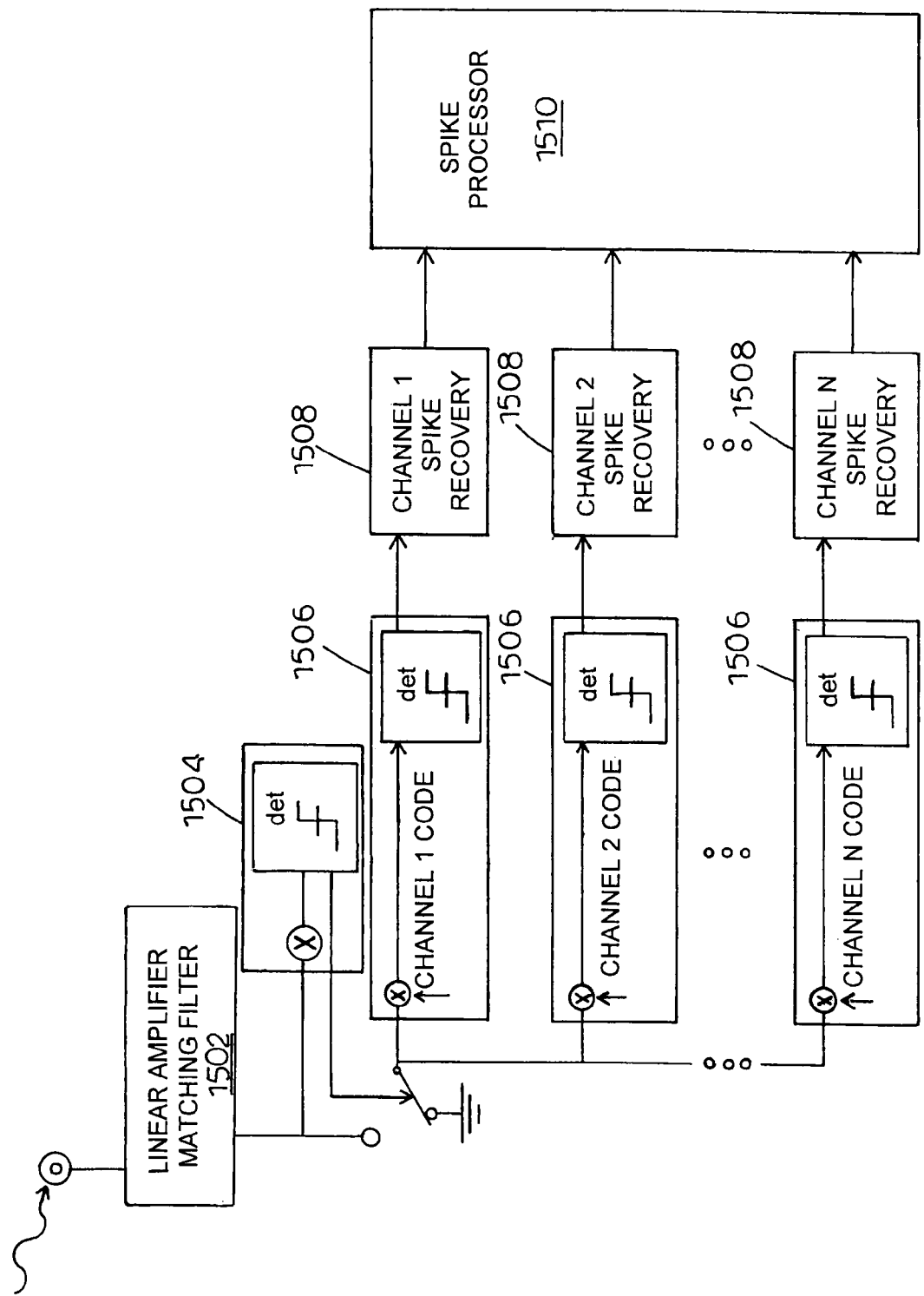
FIG. 15 is a schematic view of a signal receiver and a spike processor according to one embodiment of the present invention.

Referring to FIG. 15, a schematic view of a signal receiver, generally designated 1500, and a spike processor, generally designated 1502, according to one embodiment of the present invention is illustrated. Signal receiver 1500 can receive signal from signal transmitter 1400 of FIG. 14. Signal receiver 1500 can include a linear amplifier matching filter 1502 for receiving the transmitted signal. The received signal is passed to a sync waveform correlator and peak detector 1504 for recovering the delay/timing of each transmitted frame resulting in a pulsed waveform. The pulsed waveform is transmitted to channel data correlators 1506 for identifying the time when the data is recovered. Next, channel spike recovery components 1508 convert the channel-encoded signals to the actual single pulse output. The individual outputs are then sent to a spike processor 1510 for processing into control signals.

It will be understood that various details of the invention may be changed without departing from the scope of the invention. Furthermore, the foregoing description is for the purpose of illustration only, and not for the purpose of limitation.

What is claimed is:

1. A neural spike detection system, comprising:
   (a) a signal receiver operable to receive a plurality of neural signals comprising a neural spike and wherein the signal receiver comprises a plurality of neural sensors for detecting the neural signals from neurons;
   (b) a neural spike detector adapted to communicate with the signal receiver and detect the neural spike in the plurality of neural signals;
   (c) a transmitter in communication with the neural spike detector and operable to transmit an information signal when a neural spike is detected;
   (d) a multiplexer comprising an output and one or more inputs connected to the neural sensors for selecting a neural signal as a reference signal as the output; and
   (e) a plurality of operational amplifiers having first and second inputs, wherein the neural sensors are connected to the first inputs of the operational amplifiers and the second inputs are connected to the output of the multiplexer for providing a difference signal between the neural signals of the neural sensors and the reference signal.

2. The system of claim 1 wherein the system is an implantable neurochip comprising very large-scale integration architecture.

3. The system of claim 1 wherein the neural spike detector comprises a remote device and communicates with the signal receiver via a wireless link.

4. The system of claim 3 wherein the wireless link comprises radio frequency telemetry.

5. The system of claim 3 wherein the wireless link comprises ultra wideband radio telemetry.

6. The system of claim 3 wherein the wireless link comprises optical telemetry.

7. The system of claim 3 wherein the remote device is adapted to be worn by a subject.

8. The system of claim 1 wherein the transmitter is implantable into a subject and further includes transcutaneous telemetry for transmitting the information signal outside the subject.

9. The system of claim 1 wherein the plurality of neural sensors comprise electrodes.

10. The system of claim 1 wherein the plurality of neural sensors comprise magnetic field detectors.

11. The system of claim 1 wherein the plurality of neural sensors comprise chemical sensors.

12. The system of claim 1 wherein the signal receiver comprises amplifiers operable to amplify the plurality of neural signals.

13. The system of claim 12 further comprising a control module adapted to selectively power the amplifiers for conserving power.

14. The system of claim 12 further comprising a control module adapted to selectively control the amplification of the amplifiers.

15. The system of claim 1 further including a controller connected to the neural spike detector and operable to output control signals in response to detected neural spikes.

16. The system of claim 1 wherein the signal receiver comprises filters operable to filter predetermined frequencies in the plurality of neural signals.

17. The system of claim 16 wherein the filters are adjustable to filter different frequency ranges.

18. The system of claim 17 further comprising a control module adapted to selectively adjust the frequency ranges filtered by the filters.

19. The system of claim 16 wherein the filters are operable to filter frequencies between about 500 and about 10,000 hertz.

20. The system of claim 15 wherein the control signals are transmitted to a mechanical device.

21. The system of claim 1 further comprising a control module adapted to selectively control the multiplexer for outputting the neural signal as the reference signal.

22. The system of claim 1 further comprising one or more analog-to-digital converters connected to the operational amplifiers for converting the difference signal to a digital representation.

23. The system of claim 1 further including an indicator connected to the neural spike detector and operable to transmit a sensory signal indicating detection of a sensory input.

24. The system of claim 23 wherein the sensory input is one of touch, sound, light, and chemical stimuli.

25. The system of claim 1 further comprising a capacitor connected to the operational amplifier for reducing DC offset in the neural signal.

26. The system of claim 25 wherein the capacitor and operational amplifier are manufactured on a first and second integrated circuit, respectively.

27. The system of claim 1 further comprising a wireless power receiver adapted to wirelessly receive power from a wireless power transmitter for powering the system.

28. The system of claim 27 wherein the wireless power receiver is adapted to receive a clock signal with the power from the wireless power transmitter.

29. The system of claim 1 wherein the neural spike detector includes very large-scale integration architecture.

30. The system of claim 1 wherein the transmitter includes an encoder for encoding the information signal.

31. The system of claim 1 wherein the information signal is a digital signal.

32. The system of claim 1 wherein the transmitter transmits a pulse when a neural spike is detected in one of the plurality of neural signals.

33. The system of claim 1 wherein the transmitter transmits a first and a second pulse when a neural spike is detected on one of the plurality of neural signals, the two pulses being time-spaced by a predetermined length of time for indicating on which of the plurality of neural signals that the neural spike was detected.

34. The system of claim 1 wherein the information signal is a time multiplexed analog signal.

35. The system of claim 1 wherein the signal receiver isolates neural spikes from noise sources by employing differential recording.

36. The system of claim 1 wherein the signal receiver isolates neural spikes from noise sources with filtering and differential recording.

37. The system of claim 1 wherein the transmitter comprises a radio frequency transmitter.

38. The system of claim 1 wherein the transmitter comprises ultra wide band radio.

* * * * *